US012657717B2

(12) United States Patent
Anegondi et al.

(10) Patent No.: US 12,657,717 B2
(45) Date of Patent: Jun. 16, 2026

(54) MULTIMODAL GEOGRAPHIC ATROPHY LESION SEGMENTATION

(71) Applicant: Genentech, Inc., South San Francisco, CA (US)

(72) Inventors: Neha Sutheekshna Anegondi, South San Francisco, CA (US); Simon Shang Gao, South San Francisco, CA (US); Jiaxiang Jiang, South San Francisco, CA (US); Michael Gregg Kawczynski, South San Francisco, CA (US); Jasmine Patil, South San Francisco, CA (US); Theodore C. Spaide, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 294 days.

(21) Appl. No.: 18/304,006

(22) Filed: Apr. 20, 2023

(65) Prior Publication Data

US 2023/0342935 A1 Oct. 26, 2023

Related U.S. Application Data

(63) Continuation of application No. PCT/US2021/056327, filed on Oct. 22, 2021.
(Continued)

(51) Int. Cl.
*G06T 7/00* (2017.01)
*A61B 3/10* (2006.01)
(Continued)

(52) U.S. Cl.
CPC ............ *G06T 7/0014* (2013.01); *A61B 3/102* (2013.01); *A61B 3/1225* (2013.01); *G06T 7/174* (2017.01);
(Continued)

(58) Field of Classification Search
CPC ......... G06T 7/0014; G06T 7/174; G06T 7/62; G06T 2207/10048; G06T 2207/10064;
(Continued)

(56) References Cited

U.S. PATENT DOCUMENTS 9,241,626 B2 * 1/2016 Narasimha-Iyer ..... A61B 3/102
11,232,572 B2 * 1/2022 Chen ......................... G06T 7/11
(Continued)

FOREIGN PATENT DOCUMENTS

JP 2019531817 A 11/2019
WO 2020160839 A1 8/2020
(Continued)

OTHER PUBLICATIONS

Wu, M. et al. "Geographic atrophy segmentation in SD-OCT images using synthesized fundus autofluorescence imaging" Computer Methods and Programs in Biomedicine 182, Dec. 2019, pp. 1-10 (Year: 2019).*

(Continued)

*Primary Examiner* — Mia M Thomas

(74) *Attorney, Agent, or Firm* — Haynes and Boone, LLP

(57) ABSTRACT

A method and system for generating a geographic atrophy (GA) lesion segmentation mask corresponding to GA lesions in a retina is disclosed herein. In some embodiments, a set of fundus autofluorescence (FAF) images of a retina having one or more geographic atrophy (GA) lesions and one or both of a set of infrared (IR) images of the retina or a set of optical coherence tomography (OCT) images of the retina may be used to generate the GA lesion segmentation mask including one or more GA lesion segments corresponding to the one or more GA lesions in the retina. In some instances, a neural network may be used to generate the GA lesion segmentation mask.

38 Claims, 21 Drawing Sheets

$200$—

Related U.S. Application Data

(60) Provisional application No. 63/218,908, filed on Jul. 6, 2021, provisional application No. 63/105,105, filed on Oct. 23, 2020.

(51) Int. Cl.
*A61B 3/12* (2006.01)
*G06T 7/174* (2017.01)
*G06T 7/62* (2017.01)

(52) U.S. Cl.
CPC ...... *G06T 7/62* (2017.01); *G06T 2207/10048* (2013.01); *G06T 2207/10064* (2013.01); *G06T 2207/10101* (2013.01); *G06T 2207/20021* (2013.01); *G06T 2207/20084* (2013.01); *G06T 2207/30041* (2013.01); *G06T 2207/30096* (2013.01)

(58) Field of Classification Search
CPC . G06T 2207/10101; G06T 2207/20021; G06T 2207/20084; G06T 2207/30041; G06T 2207/30096; G06T 7/11; G06T 7/0012; A61B 3/102; A61B 3/1225
See application file for complete search history.

(56) References Cited

U.S. PATENT DOCUMENTS

| | | | |
|---|---|---|---|
| 2014/0268046 A1* | 9/2014 | Narasimha-Iyer | ........ G06T 5/70 351/246 |
| 2016/0284085 A1* | 9/2016 | Huang | .................... G06T 7/136 |
| 2016/0284103 A1* | 9/2016 | Huang | .................. A61B 3/102 |
| 2017/0224213 A1* | 8/2017 | Ishiai | ....................... A61B 3/10 |
| 2018/0003479 A1* | 1/2018 | Tomatsu | ............ G01B 9/02092 |
| 2018/0263490 A1* | 9/2018 | Jia | ........................... G06F 18/23 |
| 2020/0075155 A1* | 3/2020 | Huang | .................... G16H 30/20 |
| 2021/0003383 A1* | 1/2021 | Tsukada | ................. A61B 3/102 |
| 2021/0161376 A1* | 6/2021 | Ono | ....................... A61B 3/117 |
| 2021/0319556 A1 | 10/2021 | Chauhan | |
| 2022/0084210 A1* | 3/2022 | Manivannan | ........ G06V 10/469 |
| 2022/0207729 A1* | 6/2022 | Boyd | .................. G06V 40/197 |
| 2022/0230300 A1 | 7/2022 | Kawczynski et al. | |
| 2023/0025980 A1 | 1/2023 | Kawczynski et al. | |
| 2023/0036463 A1* | 2/2023 | Yang | ......................... G06T 7/12 |
| 2023/0135258 A1* | 5/2023 | Patil | ..................... G06T 7/0012 382/131 |
| 2023/0274531 A1* | 8/2023 | Zhu | ........................... G06T 7/10 382/128 |
| 2023/0301727 A1* | 9/2023 | Leiderman | ............. G16H 40/63 |
| 2023/0326024 A1* | 10/2023 | Yang | ..................... G06T 7/0012 382/131 |
| 2024/0038370 A1 | 2/2024 | Anegondi et al. | |
| 2024/0087120 A1* | 3/2024 | Anegondi | .............. G16H 50/20 |
| 2024/0296555 A1* | 9/2024 | Joskowicz | ........... G06T 7/0012 |
| 2024/0386546 A1* | 11/2024 | Chu | ........................ G06T 7/0012 |
| 2025/0295308 A1* | 9/2025 | Ribaric | ................ A61B 3/0025 |

FOREIGN PATENT DOCUMENTS

| | | |
|---|---|---|
| WO | 2020188007 A1 | 9/2020 |
| WO | 2020/210891 A1 | 10/2020 |

OTHER PUBLICATIONS

Mehta, S. "Y-Net: Joint Segmentation and Classi cation for Diagnosis of Breast Biopsy Images" Computer Vision and Pattern Recognition Jun. 4, 2018, pp. 1-9 (Year: 2018).*

Kikuchi et al., "A pilot study using machine learning (ML) to predict treatment outcomes in patients with neovascular age-related macular degeneration(nAMD) using phase 2 trial data." Investigative Ophthalmology & Visual Science Jun. 2021, vol. 62, 82, p. 82, 3 pages.

Dai et al., "Accurately identify nAMD patients with low Anti-VEGF treatment need by deep learning." Investigative Ophthalmology & Visual Science, Jun. 2020, vol. 61, Issue 7, p. 4218, 3 pages.

Kawczynski et al., "Development of deep learning models to predict best-corrected visual acuity from optical coherence tomography." Translational Vision Science & Technology, Sep. 9, 2020, vol. 9, No. 2, Article 51, 14 pages.

Spaide et al., "Geographic atrophy segmentation using multimodal deep learning." Translational Vision Science & Technology, Jul. 2023, vol. 12, No. 7, Article 10, 16 pages.

Wang et al., "Identification of choroidal neovascularization activity using deep learning." Investigative Ophthalmology & Visual Science, Jun. 2021, vol. 62, Issue 8, p. 2141, 3 pages.

Kikuchi et al., "Machine Learning to Predict Faricimab Treatment Outcome in Neovascular Age-Related Macular Degeneration." American Academy of Ophthalmology, Ophthalmology Science, Apr. 2024, vol. 4, No. 2, 12 pages.

Maunz et a., "Machine Learning to Predict Response to Ranibizumab in Neovascular Age-Related Macular Degeneration." American Academy of Ophthalmology, Ophthalmology Science, Dec. 2023, vol. 3, No. 4, 9 pages.

Kawczynski et al., "Prediction of best-corrected visual acuity(BCVA) from color fundus photography (CFP) using deep learning (DL)." Investigative Ophthalmology & Visual Science, Jun. 2021, vol. 62, Issue 8, p. 126, 2 pages.

International Search Report and Written Opinion mailed Mar. 4, 2022 in International Application No. PCT/US2021/056327, 12 pages.

International Preliminary Report on Patentability dated Apr. 13, 2023 from International Application No. PCT/US2021/056327, 7 pages.

Wu et al., "Geographic Atrophy Segmentation in SD-OCT Images Using Synthesized Fundus Autofluorescence Imaging", Computer Methods and Programs in Biomedicine, vol. 182, Dec. 1, 2019, 10 pages.

Arslan et al., "Deep Learning Applied to Automated Segmentation of Geographic Atrophy in Fundus Autofluorescence Images", Translational Vision Science & Technology, vol. 10, No. 8, Jul. 6, 2021, 17 pages.

Mehta et al., "Y-Net: Joint Segmentation and Classification for Diagnosis of Breast Biopsy Images", Jun. 4, 2018, 9 pages.

Tufail et al., "Objective Measurement of Reading Speed and Correlation With Patient-Reported Functional Reading Independence." Presented at the 15th EURETINA Congress, Nice, France, Sep. 17-20, 2015.

The Eye Diseases Prevalence Research Group, "Prevalence of Age-Related Macular Degeneration in the United States," Arch. Ophthalmol., Apr. 2004, vol. 122, pp. 564-572.

Merck, "The Merck Manual. Age-Related Macular Degeneration," Section 3, Chapter 36, retrieved from Wayback Machine on Sep. 22, 2023. Retrieved from https://www.merck.com/pubs/mmanual_ha/sec3/ch36/ch36d.html.

Ronneberger et al., "U-Net: Convolutional Networks for Biomedical Image Segmentation," Medical Image Computing and Computer-Assisted Intervention (MICCAI), Springer, LNCS, vol. 9351, pp. 234-241, 2015.

Wu et al., "Group Normalization," Proceedings of the European Conference on Computer Vision (ECCV), 2018, pp. 3-19.

Patil et al., "Change in Geographic Atrophy Lesion Area: Comparison Between Fully Automatic Segmentation and Semi-Automatic Segmentation," ARVO Imaging in the Eye Conference Abstract, vol. 61, Issue 9, Jul. 2020.

Flaxman et a., "Global Causes of Blindness and Distance Vision Impairment 1990-2020: A Systematic Review and Meta-Analysis," Lancet Glob Health, vol. 5, No. 12, Dec. 2017, pp. e1221-e1234.

Clemons et al., "Risk Factors for the Incidence of Advanced Age-Related Macular Degeneration in the Age-Related Eye Disease Study (AREDS) AREDS Report No. 19," Ophthalmology, vol. 112, No. 4, 2005, pp. 533-539.

Sarks et al., "Evolution of Geographic Atrophy of the Retinal Pigment Epithelium," Eye, vol. 2, pp. 552-577, 1988.

Holz et al., "Efficacy and Safety of Lampalizumab for Geographic Atrophy Due to Age-Related Macular Degeneration: Chroma and

(56) References Cited

OTHER PUBLICATIONS

Spectri Phase 3 Randomized Clinical Trials," JAMA Ophthalmology, vol. 136, No. 6, 2018, pp. 666-677.

Yehoshua et al., "Systemic Complement Inhibition with Eculizumab for Geographic Atrophy in Age-Related Macular Degeneration: the Complete Study," Ophthalmology, vol. 121, No. 3, 2014, pp. 693-701.

Fleckenstein et al., "The Progression of Geographic Atrophy Secondary to Age-Related Macular Degeneration," Ophthalmology, vol. 125, No. 3, 2018, pp. 369-390.

Göbel et al., "Imaging Geographic Atrophy in Age-Related Macular Degeneration," Ophthalmologica, vol. 226, No. 4, 2011, pp. 182-190.

Schmitz-Valckenberg et al., "Fundus Autofluorescence Imaging: Review and Perspectives," Retina, vol. 28, No. 3, 2008, pp. 385-409.

Csaky et al., "Report From the NEI/FDA Endpoints Workshop on Age-Related Macular Degeneration and Inherited Retinal Diseases," Investigative Ophthalmology and Visual Science, Jul. 2017, vol. 58, No. 9, pp. 3456-3463.

Holmen et al., "Precursors and Development of Geographic Atrophy with Autofluorescence Imaging: Age-Related Eye Disease Study 2 Report No. 18," Ophthalmology Retina, vol. 3, No. 9, 2019, pp. 724-733.

Hu et al., "Automated Segmentation of Geographic Atrophy in Fundus Autofluorescence Images Using Supervised Pixel Classification," Journal of Medical Imaging, vol. 2, No. 1, Jan.-Mar. 2015, pp. 014501-1-014501-7.

Schmitz-Valckenberg et al., "Semiautomated Image Processing Method for Identification and Quantification of Geographic Atrophy in Age-Related Macular Degeneration," Investigative Ophthalmology & Visual Science, Sep. 2011, vol. 52, No. 10, pp. 7640-7646.

Devisetti et al., "Geographic Atrophy Segmentation in Infrared and Autofluorescent Retina Images Using Supervised Learning," 33rd Annual International Conference of the IEEE Engineering in Medicine and Biology Aug. 30-Sep. 3, 2011, pp. 3958-3961.

Ji et al., "Beyond Retinal Layers: A Deep Voting Model for Automated Geographic Atrophy Segmentation in SD-OCT Images," Translational Vision Science & Technology, vol. 7, No. 1, 2018, 21 pages.

Wu et al., "Geographic Atrophy Segmentation in SD-OCT Images Using Synthesized Fundus Autofluorescence Imaging," Computer Methods and Programs in Biomedicine, Dec. 2019, vol. 182, No. 105101, 10 pages.

Holekamp et al., "Natural History of Geographic Atrophy Secondary to Age-Related Macular Degeneration: Results from the Prospective Proxima A and B Clinical Trials," Ophthalmology, vol. 127, No. 6, Jun. 2020, pp. 769-783.

Patil et al., "Change in Geographic Atrophy Lesion Area: Comparison Between Fully Automatic Segmentation and Semi-Automatic Segmentation," Investigative Ophthalmology & Visual Science, Jul. 2020, vol. 61, No. 9, PB0062.

Anegondi et al., "Evaluation of Shape-Descriptive and Texture Features As Potential Prognostic Variables in Progression of Geographic Atrophy", Investigative Ophthalmology & Visual Science, Jul. 2019, vol. 60, No. 9, pp. 1906.

Pfau et al., "Prognostic Value of Shape-Desscriptive Factors for the Progression of Geographic Atrophy Secondary to Age-Related Macular Degeneration," Retina, 2019, vol. 39, No. 8, pp. 1527-1539.

Patil et al., "Geographic Atrophy Lesion Segmentation Using a Deep Learning Network (U-Net)," Investigative Ophthalmology & Visual Science, Jul. 2019, vol. 60. No. 9, p. 1459.

Patil et al., "Increased Expression of the Chronic ER Stress-Induced Transcriptional Factor, ATF4 Leads to Glaucoma by Promoting Protein Synthesis and ER Client Protein Load | IOVS," Investigative Ophthalmology & Visual Science, Jun. 2020, vol. 61, Issue 7, PB0062.

Spaide et al., "Analysis of Numerical Feature Extraction From Automated Geographic Atrophy Segmentation," ARVO Annual Meeting Abstract, Jun. 2021, vol. 62, pp. 2124.

* cited by examiner

200

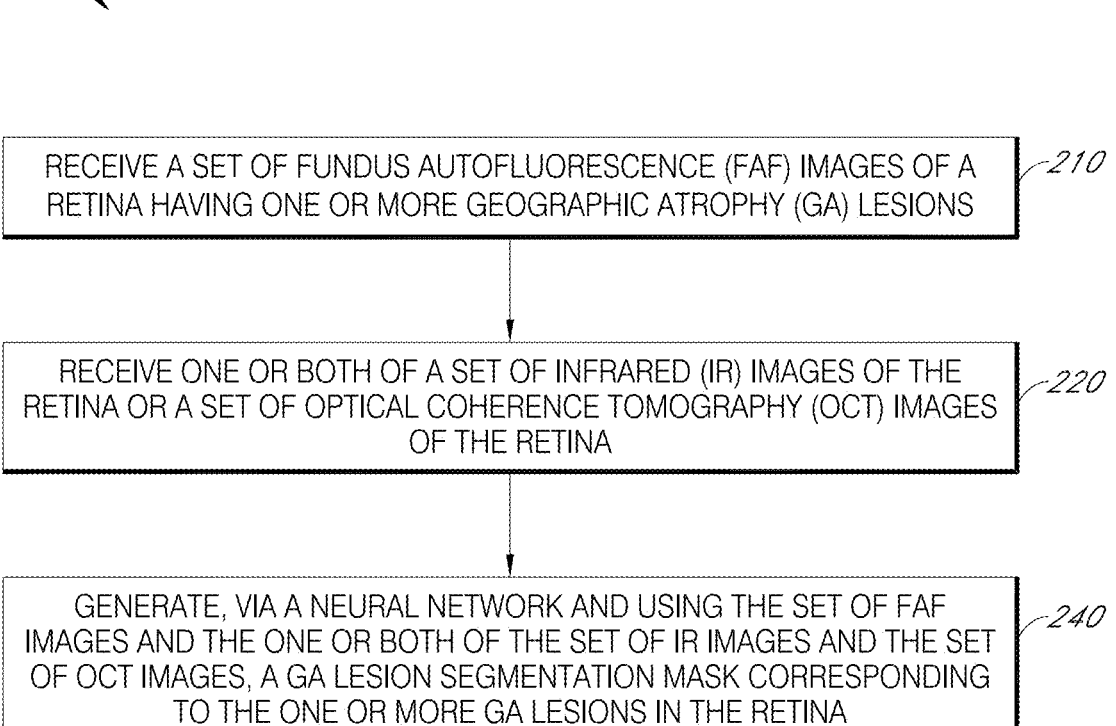

RECEIVE A SET OF FUNDUS AUTOFLUORESCENCE (FAF) IMAGES OF A RETINA HAVING ONE OR MORE GEOGRAPHIC ATROPHY (GA) LESIONS ⟋210

RECEIVE ONE OR BOTH OF A SET OF INFRARED (IR) IMAGES OF THE RETINA OR A SET OF OPTICAL COHERENCE TOMOGRAPHY (OCT) IMAGES OF THE RETINA ⟋220

GENERATE, VIA A NEURAL NETWORK AND USING THE SET OF FAF IMAGES AND THE ONE OR BOTH OF THE SET OF IR IMAGES AND THE SET OF OCT IMAGES, A GA LESION SEGMENTATION MASK CORRESPONDING TO THE ONE OR MORE GA LESIONS IN THE RETINA ⟋240

FIG. 2

MULTIMODAL GEOGRAPHIC ATROPHY LESION SEGMENTATION

CROSS-REFERENCE TO RELATED APPLICATIONS

The present application is a continuation of International Application No. PCT/US2021/056327 filed Oct. 22, 2021, which claims priority to and the benefit of the U.S. Provisional Patent Application No. 63/105,105, filed Oct. 23, 2020, and U.S. Provisional Patent Application No. 63/218,908, filed Jul. 6, 2021, both titled "Multimodal Geographic Atrophy Lesion Segmentation," all of which are hereby incorporated by reference in their entirety as if fully set forth below and for all applicable purposes.

FIELD

This description is generally directed towards evaluating geographic atrophy in a retina. More specifically, this description provides methods and systems for evaluating geographic atrophy using images from multiple modalities including fundus autofluorescence (FAF) images, and one or both of near infrared (NIR) images and optical coherence tomography (OCT) images.

BACKGROUND

Age-related macular degeneration (AMD) is a leading cause of vision loss in patients 50 years or older. Geographic atrophy (GA) is one of two advanced stages of AMD and is characterized by progressive and irreversible loss of choriocapillaries, retinal pigment epithelium (RPE), and photoreceptors. The diagnosis and monitoring of GA lesion enlargement may be performed using fundus autofluorescence (FAF) images that are obtained by confocal scanning laser ophthalmoscopy (cSLO). This type of imaging technology, which shows topographic mapping of lipofuscin in RPE, can be used to measure the change in GA lesions over time. On FAF images, GA lesions appear as regions of hypoautofluorescence with sharply demarcated boundaries, due to loss of RPE and thus lipofuscin. However, quantifying GA lesions on FAF images may be challenging due to naturally occurring low intensities at the fovea. Further, quantifying GA lesions using FAF images is typically a manual process that is more time-consuming and more prone to inter-observer and intra-observer variability than desired. Thus, it may be desirable to have one or more methods, systems, or both that recognize and take into account one or more of these issues.

SUMMARY

Some embodiments of the present disclosure include a method comprising receiving a set of fundus autofluorescence (FAF) images of a retina having one or more geographic atrophy (GA) lesions. The method further comprises receiving one or both of a set of infrared (IR) images of the retina or a set of optical coherence tomography (OCT) images of the retina; and generating, using the set of FAF images and the one or both of the set of IR images or the set of OCT images, a GA lesion segmentation mask including one or more GA lesion segments corresponding to the one or more GA lesions in the retina.

In some embodiments, a system, comprises a non-transitory memory; and a hardware processor coupled with the non-transitory memory and configured to read instructions from the non-transitory memory to cause the system to perform operations. In some instances, the operations comprise receiving a set of FAF images of a retina having one or more GA lesions; receiving one or both of a set of IR images of the retina or a set of OCT images of the retina; and generating, using the set of FAF images and the one or both of the set of IR images or the set of OCT images, a GA lesion segmentation mask including one or more GA lesion segments corresponding to the one or more GA lesions in the retina.

Some embodiments of the present disclosure disclose a non-transitory computer-readable medium (CRM) having stored thereon computer-readable instructions executable to cause a computer system to perform operations comprising receiving a set of FAF images of a retina having one or more GA lesions. In some embodiments, the operations further comprise receiving one or both of a set of IR images of the retina or a set of OCT images of the retina; and generating, using the set of FAF images and the one or both of the set of IR images or the set of OCT images, a GA lesion segmentation mask including one or more GA lesion segments corresponding to the one or more GA lesions in the retina.

Other aspects, features, and embodiments of the present invention will become apparent to those of ordinary skill in the art, upon reviewing the following description of specific, exemplary embodiments of the present invention in conjunction with the accompanying figures. While features of the present invention may be discussed relative to certain embodiments and figures below, all embodiments of the present invention can include one or more of the advantageous features discussed herein. In other words, while one or more embodiments may be discussed as having certain advantageous features, one or more of such features may also be used in accordance with the various embodiments of the invention discussed herein. In similar fashion, while exemplary embodiments may be discussed below as device, system, or method embodiments it should be understood that such exemplary embodiments can be implemented in various systems and methods.

BRIEF DESCRIPTION OF THE DRAWINGS

For a more complete understanding of the principles disclosed herein, and the advantages thereof, reference is now made to the following descriptions taken in conjunction with the accompanying drawings, in which:

FIG. 2 is a flowchart of a process for evaluating geographic atrophy in accordance with various embodiments.

Figure 1:
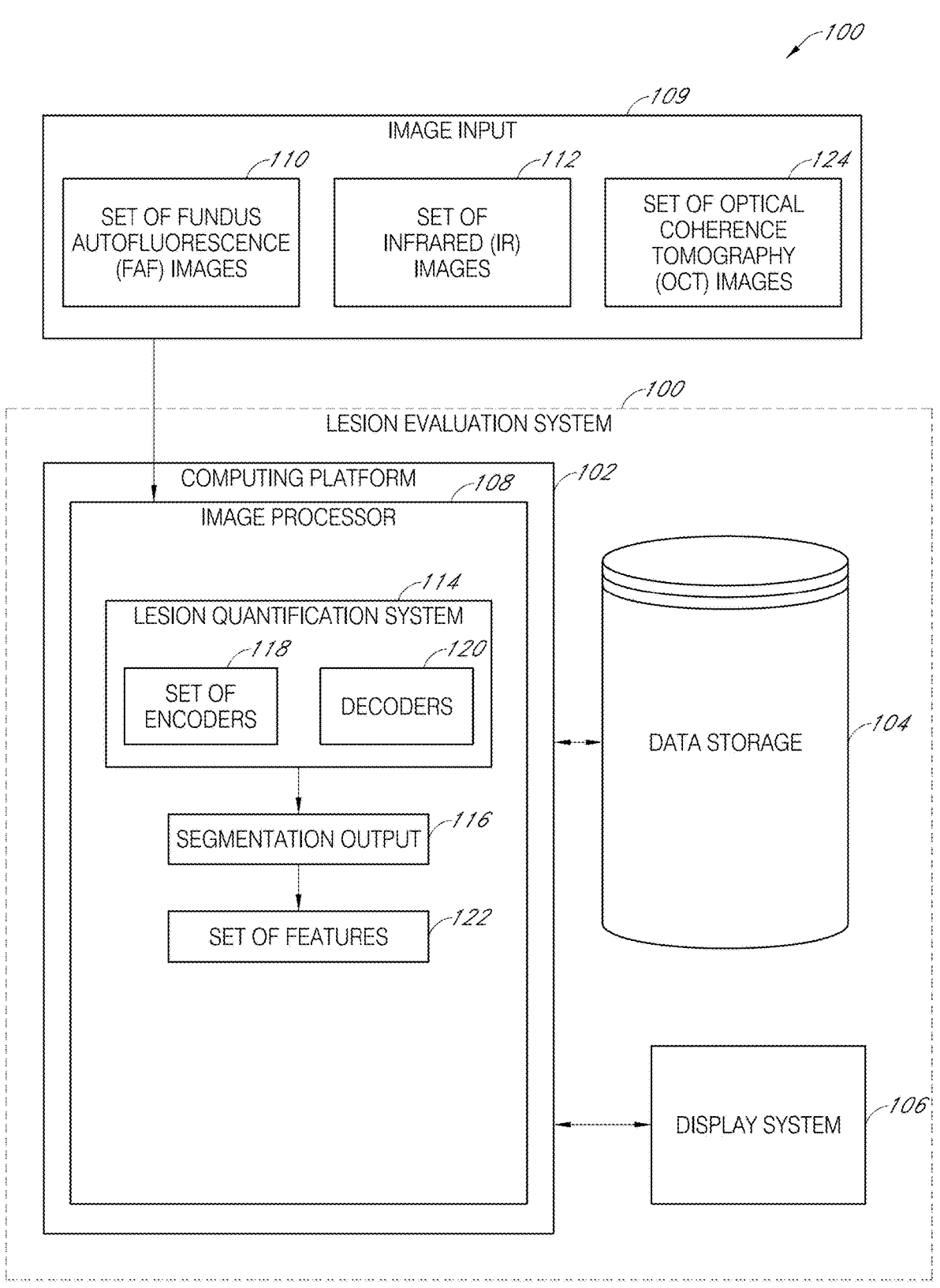
FIG. 1 is a block diagram of a lesion evaluation system in accordance with various embodiments.

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the same reference numbers will be used throughout the drawings to refer to the same or like parts. Moreover, it should be appreciated that the drawings are not intended to limit the scope of the present teachings in any way.

DETAILED DESCRIPTION

I. Overview

Current methods for evaluating geographic atrophy (GA), which is characterized by progressive and irreversible loss of photoreceptors, retinal pigment epithelium (RPE) and choriocapillaris, include analyzing fundus autofluorescence (FAF) images to evaluate GA lesions, which are detected and demarcated due to reduced autofluorescence caused by loss of RPE cells and lipofuscin, an intrinsic fluorophore. The delineation or segmentation of the GA lesions includes creating a pixel-wise mask for the GA lesion in the FAF images. The pixel-wise mask identifies each pixel as belonging to one of at least two different classes. As one example, each pixel may be assigned to either a first class corresponding to a GA lesion or a second class that does not correspond to the GA lesion. In this manner, pixels assigned to the first class identify the GA lesion. This type of segmentation may be referred to as GA segmentation.

Segmentation of GA lesions in FAF images can be manual or automated. Manual measurements of GA lesions from FAF images by human graders can give excellent reproducibility with experienced graders, but the manual delineation of GA areas can be time-consuming and subject to inter- and intra-grader variability, especially with less-experienced graders, and also to variations between different reading centers. Some methods include using software, which may be semi-automated, to segment GA lesions in FAF images. However, trained readers of FAF images may still be needed for high quality segmentation: for example, human user input may be used to precisely outline the lesion borders. Accordingly, there is a need for methods and systems that allow for fully automated segmentation of FAF images of GA lesions in retinas.

Artificial intelligence (AI), and in particular machine learning and deep learning systems, can be configured to automatically segment GA lesions or assess shape-descriptive features of GA progression from FAF images of retinas. AI systems can detect and quantify GA lesions at least as accurately as human graders but much faster and more cost-effectively, especially when processing large datasets. For example, segmentations performed by algorithms using k-nearest-neighbor (k-NN) pixel classifiers, Fuzzy c-means (a clustering algorithm), or deep convolutional neural networks (CNNs) can have good agreement with manual segmentation performed by trained graders. That said, FAF images tend to exhibit low intensity at the portion of an image showing a fovea of a subject's retina. The low intensity means that lesion boundaries or areas may be obscured or difficult to distinguish. As a result, it is difficult to accurately quantify GA lesions from FAF images, whether using AI or manual annotations.

At the same time, various other imaging modalities are sometimes used in clinical trials or clinical practice, to capture retinal images. For instance, infrared reflectance (IR) imaging and optical coherence tomography (OCT) imaging are other common imaging methods. At present, the imaging modalities are used independently and mutually exclusively from one another in assessing GA progression.

The present embodiments aim to leverage beneficial characteristics of retinal images provided by various imaging modalities, in efforts to improve assessments of GA progression. GA lesion segmentation results obtained from retina images that are combinations of various imaging techniques can be more accurate and provide additional information when compared to segmentation results obtained from unimodal image inputs. Thus, the methods and systems of the present disclosure allow automated segmentation of GA lesions on images using a multimodal approach and a neural network system. This multimodal approach uses FAF images, and one or both of IR (e.g., near-infrared (NIR)) images and OCT images (e.g., en-face OCT images).

For example, near-infrared reflectance imaging uses longer wavelengths than FAF to avoid media opacities, neurosensory layers and macular luteal pigments. As such, GA lesions may appear brighter than non-atrophic regions. In such cases, NIR images may complement FAF images to facilitate the detection of foveal lesion boundaries, which can be more difficult with FAF alone due to lower image contrast/intensities at the fovea. In some instances, OCT en-face images, which are transverse images of retinal and choroidal layers at specified depths, may also be segmented in combination with FAF images, and in some cases, with NIR images as well. Such multimodal approach where images obtained from multiple imaging techniques are used as image inputs of GA lesion segmentation AI system (e.g., a neural network system) may facilitate the generation of improved segmentation results, as discussed above, but also can be used for evaluating GA lesion enlargement over time, i.e., longitudinally.

In addition, the present disclosure provides systems and methods of automated segmentation of GA lesions using machine learning. In one embodiment, the present disclosure provides systems and methods of segmentation on images using a multimodal approach and a neural network system. That is, for example, neural network systems may receive multimodal image inputs, i.e., image inputs including retinal images from more than one modalities (e.g., FAF images. NIR images, OCT images, etc.) may produce or generate GA lesion segmentation results that may be more accurate and informative compared to segmentation results from single modality image inputs. This may be because retinal images from one modality may include information about the depicted retina that may not be available from another modality.

The neural network system may include but not limited to a convolutional neural network (CNN) system, deep learning system (e.g., U-Net deep learning neural network, Y-Net deep learning neural network, etc.), and/or the like. Such multimodal approaches that utilize neural network systems for segmenting retinal images facilitate accurate segmentation of GA lesions as well as accurate and efficient quantification of the GA lesions longitudinally, i.e., accurate and efficient monitoring of GA lesion enlargement over time.

For example, IR images and, in particular, NIR images, may provide a greater field of view than OCT en-face images. Further, using IR images and, more particularly, NIR images, in combination with FAF images provides greater resolution and clarity with respect to segmenting the GA lesion. This greater resolution and clarity facilitate improved segmentation of GA lesions from retinal images, which in turn facilitates improved feature extraction. For instance, features such as but not limited to boundaries, shape, texture, etc., of a GA lesion may be more accurately identified. This improved feature extraction, in turn, allows improved overall longitudinal monitoring of a GA lesion, which can be important to evaluating disease progression, therapeutic regimen effects, or both.

For example, the correlation of actual GA lesion enlargement from a baseline point in time to a later point in time (e.g., 6 months, 12 months, etc.) with the GA lesion enlargement estimated via the embodiments disclosed herein (i.e., using both FAF images and one or both of IR images, in particular, NIR images, and OCT images) may be higher than the correlation provided with some of the currently available methods. In some cases, the embodiments described herein enable improved correlation with longer time intervals. For example, using both FAF and IR images and in particular NIR images, the correlation provided for the interval of a baseline point in time to 12 months may be greater than the correlation provided for the interval of the baseline point in time to 6 months.

II. Definitions

The disclosure is not limited to these exemplary embodiments and applications or to the manner in which the exemplary embodiments and applications operate or are described herein. Moreover, the figures may show simplified or partial views, and the dimensions of elements in the figures may be exaggerated or otherwise not in proportion.

In addition, as the terms "on," "attached to," "connected to," "coupled to," or similar words are used herein, one element (e.g., a component, a material, a layer, a substrate, etc.) can be "on," "attached to," "connected to," or "coupled to" another element regardless of whether the one element is directly on, attached to, connected to, or coupled to the other element or there are one or more intervening elements between the one element and the other element. In addition, where reference is made to a list of elements (e.g., elements a, b, c), such reference is intended to include any one of the listed elements by itself, any combination of less than all of the listed elements, and/or a combination of all of the listed elements. Section divisions in the specification are for ease of review only and do not limit any combination of elements discussed.

The term "subject" may refer to a subject of a clinical trial, a person undergoing treatment, a person undergoing therapies, a person being monitored for remission or recovery, a person undergoing a preventative health analysis (e.g., due to their medical history), a person suffering from GA, or any other person or patient of interest. In various cases, "subject" and "patient" may be used interchangeably herein.

Unless otherwise defined, scientific and technical terms used in connection with the present teachings described herein shall have the meanings that are commonly understood by those of ordinary skill in the art. Further, unless otherwise required by context, singular terms shall include pluralities and plural terms shall include the singular. Generally, nomenclatures utilized in connection with, and techniques of, chemistry, biochemistry, molecular biology, pharmacology and toxicology are described herein are those well-known and commonly used in the art.

As used herein, "substantially" means sufficient to work for the intended purpose. The term "substantially" thus allows for minor, insignificant variations from an absolute or perfect state, dimension, measurement, result, or the like such as would be expected by a person of ordinary skill in the field but that do not appreciably affect overall performance. When used with respect to numerical values or parameters or characteristics that can be expressed as numerical values, "substantially" means within ten percent.

As used herein, the term "about" used with respect to numerical values or parameters or characteristics that can be expressed as numerical values means within ten percent of the numerical values. For example, "about 50" means a value in the range from 45 to 55, inclusive.

The term "ones" means more than one.

As used herein, the term "plurality" can be 2, 3, 4, 5, 6, 7, 8, 9, 10, or more.

As used herein, the term "set of" means one or more. For example, a set of items includes one or more items.

As used herein, the phrase "at least one of," when used with a list of items, means different combinations of one or more of the listed items may be used and only one of the items in the list may be needed. The item may be a particular object, thing, step, operation, process, or category. In other words, "at least one of" means any combination of items or number of items may be used from the list, but not all of the items in the list may be required. For example, without limitation, "at least one of item A, item B, or item C" means item A; item A and item B; item B; item A, item B, and item C; item B and item C; or item A and C. In some cases, "at least one of item A, item B, or item C" means, but is not limited to, two of item A, one of item B, and ten of item C; four of item B and seven of item C; or some other suitable combination.

As used herein, a "model" may include one or more algorithms, one or more mathematical techniques, one or more machine learning algorithms, or a combination thereof.

As used herein, "machine learning" may include the practice of using algorithms to parse data, learn from it, and then make a determination or prediction about something in the world. Machine learning uses algorithms that can learn from data without relying on rules-based programming.

As used herein, an "artificial neural network" or "neural network" (NN) may refer to mathematical algorithms or computational models that mimic an interconnected group of artificial neurons that processes information based on a connectionistic approach to computation. Neural networks, which may also be referred to as neural nets, can employ one or more layers of nonlinear units to predict an output for a received input. Some neural networks include one or more hidden layers in addition to an output layer. The output of each hidden layer is used as input to the next layer in the network, i.e., the next hidden layer or the output layer. Each layer of the network generates an output from a received input in accordance with current values of a respective set of parameters. In the various embodiments, a reference to a "neural network" may be a reference to one or more neural networks.

A neural network may process information in two ways; when it is being trained it is in training mode and when it puts what it has learned into practice it is in inference (or prediction) mode. Neural networks learn through a feedback process (e.g., backpropagation) which allows the network to adjust the weight factors (modifying its behavior) of the individual nodes in the intermediate hidden layers so that the output matches the outputs of the training data. In other words, a neural network learns by being fed training data (learning examples) and eventually learns how to reach the correct output, even when it is presented with a new range or set of inputs. A neural network may include, for example, without limitation, at least one of a Feedforward Neural Network (FNN), a Recurrent Neural Network (RNN), a Modular Neural Network (MNN), a Convolutional Neural Network (CNN), a Residual Neural Network (ResNet), an Ordinary Differential Equations Neural Networks (neural-ODE), or another type of neural network.

As used herein, a "lesion" may include a region in an organ or tissue that has suffered damage via injury or disease. This region may be a continuous or discontinuous region. For example, as used herein, a lesion may include multiple regions. A GA lesion is a region of the retina that has suffered chronic progressive degeneration. As used herein, a GA lesion may include one lesion (e.g., one continuous lesion region) or multiple lesions (e.g., discontinuous lesion region comprised of multiple, separate lesions).

As used herein, a "total lesion area" may refer to an area (including a total area) covered by a lesion, whether that lesion be a continuous region or a discontinuous region.

As used herein, "longitudinal" may refer to over a period of time. The period of time may be in days, weeks, months, years, or some other measure of time.

As used herein, an "encoder" may include a type of neural network that learns to efficiently encode data (e.g., one or more images) into a vector of parameters having a number of dimensions. The number of dimensions may be preselected.

As used herein, a "decoder" may include a type of neural network that learns to efficiently decode a vector of parameters having a number of dimensions (e.g., a number of preselected dimensions) into output data (e.g., one or more images or image masks).

As used herein, a "mask" may include a type of image in which each pixel of the image has one of at least two different preselected potential values.

III. Geographic Atrophy (GA) Lesion Segmentation

FIG. 1 is a block diagram of a lesion evaluation system 100 in accordance with various embodiments. Lesion evaluation system 100 is used to evaluate geographic atrophy (GA) lesions in the retinas of subjects. Lesion evaluation system 100 includes computing platform 102, data storage 104, and display system 106. Computing platform 102 may take various forms. In one or more embodiments, computing platform 102 includes a single computer (or computer system) or multiple computers in communication with each other. In other examples, computing platform 102 takes the form of a cloud computing platform.

Data storage 104 and display system 106 are each in communication with computing platform 102. In some examples, data storage 104, display system 106, or both may be considered part of or otherwise integrated with computing platform 102. Thus, in some examples, computing platform 102, data storage 104, and display system 106 may be separate components in communication with each other, but in other examples, some combination of these components may be integrated together.

Lesion evaluation system 100 includes image processor 108, which may be implemented using hardware, software, firmware, or a combination thereof. In one or more embodiments, image processor 108 is implemented in computing platform 102.

Image processor 108 receives image input 109 for processing. In one or more embodiments, image input 109 includes set of fundus autofluorescence (FAF) images 110, and one or both of a set of infrared (IR) images 112 and a set of optical coherence tomography (OCT) images 124. In one or more embodiments, set of IR images 112 is a set of near-infrared (NIR) images. In one or more embodiments, image input 109 includes images generated by a same imaging device. For example, any combination of the set of FAF images 110, the set of IR images 112 and/or the set of OCT images 124 may be generated by the same imaging device. In one or more embodiments, any one of the set of FAF images 110, the set of IR images 112 and/or the set of OCT images 124 can be unregistered images. However, in other embodiments, any one of the set of FAF images 110, the set of IR images 112 and/or the set of OCT images 124 may be registered images.

Image processor 108 processes image input 109 (e.g., the set of FAF images 110, the set of IR images 112 and/or the set of OCT images 124) using lesion quantification system 114 to generate segmentation output 116 corresponding to a GA lesion. Lesion quantification system 114 may include any number of or combination of neural networks. In one or more embodiments, lesion quantification system 114 takes the form of a convolutional neural network (CNN) system that includes one or more neural networks. Each of these one or more neural networks may itself be a convolutional neural network. In some instances, lesion quantification system 114 may be a deep learning neural network system. For example, lesion quantification system 114 may be a Y-Net deep learning neural network, as discussed in more detail with reference to FIGS. 4A-4B. As another example, lesion quantification system 114 may be a U-Net deep learning neural network, as discussed in more detail with reference to FIGS. 3A-3B.

In various embodiments, lesion quantification system 114 may include a set of encoders 118 and decoder 120. In one or more embodiments, set of encoders 118 includes a single encoder, while in other embodiments, set of encoders 118 includes multiple encoders. In various embodiments, each encoder of set of encoders 118, as well as decoder 120, may be implemented via a neural network, which may, in turn, be comprised of one or more neural networks. In one or more embodiments, decoder 120 and each encoder of set of encoders 118 is implemented using a CNN. In one or more embodiments, set of encoders 118 and decoder 120 are implemented as a Y-Net (Y-shaped) neural network system or a U-Net (U-shaped) neural network system. For example, the lesion quantification system 114 can be a Y-Net neural network system having multiple encoders (e.g., two encoders) and less number of decoders than the number of encoders (e.g., one decoder). As another example, the lesion quantification system 114 can be a U-Net neural network system having equal number of encoders and decoders, e.g., a single encoder and a single decoder.

Figure 6A:
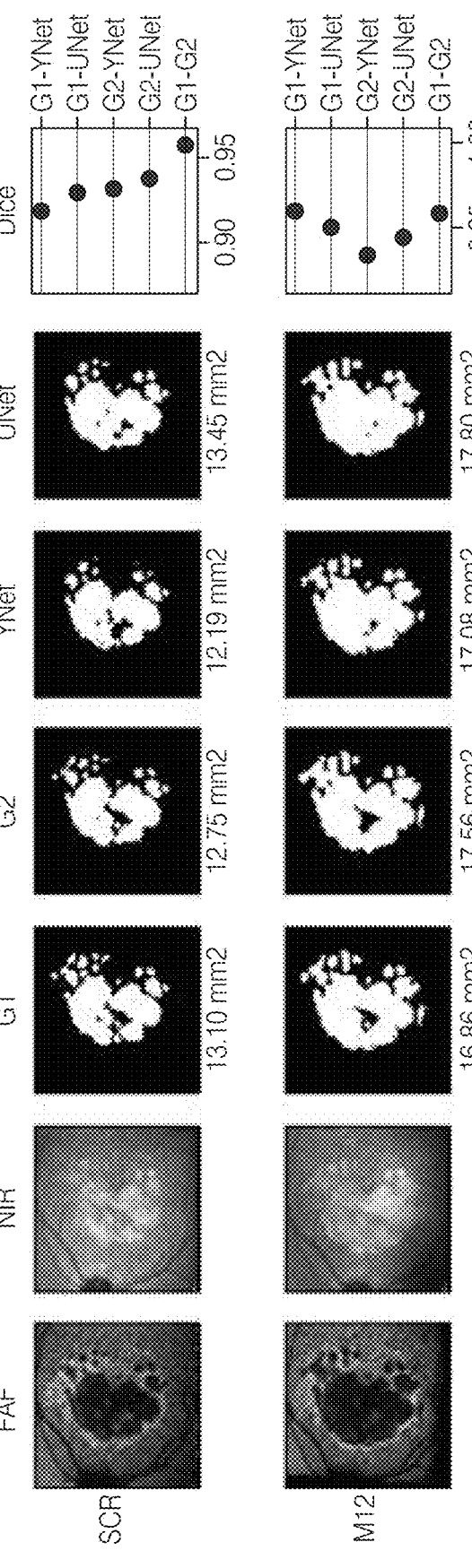
FIGS. 6A-6B illustrate example segmentation results of FAF images and NIR images using Y-Net and U-net deep learning neural networks in accordance with various embodiments.
Figure 6B:
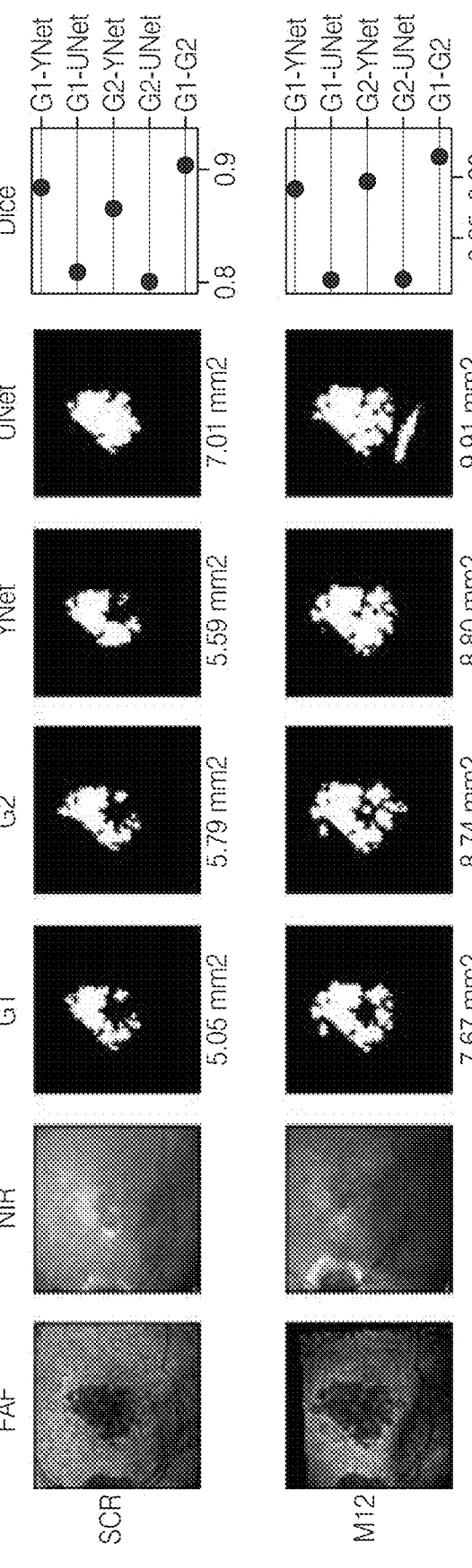

Segmentation output 116 generated by lesion quantification system 114 includes one or more segmentation masks. Each segmentation mask provides a pixel-wise evaluation of a region of a retina. For example, a segmentation mask in segmentation output 116 may be a binary image in which each pixel has one of two values. As one specific example, the segmentation mask may be a binary image in black and white in which the white indicates an area identified as the GA lesion. Non-limiting examples of segmentation mask depicting GA lesions are shown in FIGS. 6A-6B.

In one or more embodiments, lesion quantification system 114 is used to generate a preliminary probability map image in which each pixel has an intensity ranging from 0 to 1. Pixel intensities closer to 1 are more likely to be the GA lesion. Lesion quantification system 114 may include a thresholding module that applies a threshold to the preliminary probability map to produce a segmentation mask in the form of a binary probability map. For example, any pixel intensity in the preliminary probability map at or above the threshold (e.g., 0.5, 0.75, etc.) may be assigned an intensity of "1," while any pixel intensity in the preliminary probability map below the threshold may be assigned an intensity of "0." In this manner, segmentation output 116 includes a binary segmentation mask that identifies areas identified as the GA lesion.

In various embodiments, image processor 108 (or another agent or module implemented within computing platform 102) uses segmentation output 116 to generate a quantitative assessment of the GA lesion. For example, image processor 108 may use segmentation output 116 to extract set of features 122 corresponding to GA lesion. Set of features 122 may be used to evaluate the GA lesion (e.g., longitudinally). For example, the set of FAF images 110, the set of IR images 112 and/or the set of OCT images 124 may include corresponding images for the same or substantially same (e.g., within the same hour, within the same day, within the same 1-3 days, etc.) points in time. In one or more embodiments, each corresponding FAF images, and one or both of IR images and OCT images may result in a corresponding segmentation mask in segmentation output 116. Set of features 122 extracted from each of the different segmentation masks generated may provide or allow a longitudinal quantitative assessment of the GA lesion over time.

Set of features 122 may include, for example, without limitation, shape, texture, a boundary line or border map, a number of lesions, a total lesion area (i.e., the area of the lesions when considered as a combined or single lesion component), a total lesion perimeter (i.e., perimeter of the single lesion component), a Feret diameter of the single lesion component, an excess rim intensity (e.g., difference between mean intensity in a 0.5-mm rim around the lesion minus the mean intensity in a 0.5-to-1 mm rim around the lesion), circularity of the total lesion area, a metric indicating a subject's current or prospective/predicted GA progression, or a combination thereof. These different types of features may be used to quantitatively assess the GA lesion over time. For example, for a segmentation mask in segmentation output 116, the number of lesions may be the number of discontinuous regions or areas identified in the segmentation mask that form the GA lesion. The total lesion area may be identified as an area or space occupied by the one or more lesions identified, including the total area or space occupied by the lesion(s). The total lesion perimeter may be, for example, the perimeter of a general area or space occupied by the one or more lesions. In other examples, the total lesion perimeter may be the sum of the individual perimeters for the one or more lesions. The metric indicating a subject's current or prospective/predicted GA progression. In some instances, the metric may be computed from any set of features 122 extracted from the segmentation masks including, for example, shape, texture, a boundary line or border map, a number of lesions, a total lesion area (i.e., the area of the lesions when considered as a combined or single lesion component), a total lesion perimeter (i.e., perimeter of the single lesion component), a Feret diameter of the single lesion component, an excess rim intensity (e.g., difference between mean intensity in a 0.5-mm rim around the lesion minus the mean intensity in a 0.5-to-1 mm rim around the lesion), circularity of the total lesion area, or a combination thereof.

In one or more embodiments, a first segmentation mask in the segmentation output 116 may correspond to a baseline point in time, a second segmentation mask in the segmentation output 116 may correspond to 6 months after the baseline, and a third segmentation mask in the segmentation output 116 may correspond to 12 months after the baseline. Set of features 122 (e.g., shape, texture, the number of lesions, the total lesion area, the total lesion perimeter, Feret diameter, excess rim intensity, circularity of the lesion area, etc.) may be identified for each of the first, second and third segmentation masks. Thus, set of features 122 may be used to quantitatively assess the GA lesion over the period of time between the baseline point of time and 12 months.

In some embodiments, set of features 122 includes a feature that corresponds to a range of time. With respect to the above example describing the first, second, and third segmentation masks, set of features 122 may include an enlargement rate or growth rate for the GA lesion over the period of 6 months, over the period of 12 months, or both. The rate of change in lesion area, i.e., the enlargement rate, may be computed using one or more other identified features. For example, the enlargement rate for the period of 6 months may be computed based on a difference between the total lesion area extracted for the first segmentation mask and the total lesion area extracted for the second segmentation mask. The enlargement rate for the period of 12 months may be computed based on a difference between the total lesion area extracted for the first segmentation mask and the total lesion area extracted for the third segmentation mask. In this manner, set of features 122 may include one or more features that are computed based on one or more other features in set of features 122.

Segmentation output 116 may include as many segmentation masks as desired to evaluate the GA lesion over a selected period of time (e.g., 3 months, 6 months, 12 months, 18 months, etc.). Further, segmentation output 116 may include as many segmentation masks as desired to evaluate the GA lesion at the desired time intervals within the selected period of time. The desired time intervals may be constant or different time intervals. In one or more embodiments, segmentation output 116 includes a segmentation mask for every 10 days within a 12-month period.

FIG. 2 is a flowchart of a process 200 for evaluating a geographic atrophy lesion in accordance with various embodiments. In various embodiments, process 200 is implemented using the lesion evaluation system 100 described in FIG. 1.

Step 210 includes receiving a set of fundus autofluorescence (FAF) images of a retina having one or more geographic atrophy (GA) lesions.

Step 220 includes receiving one or both of a set of infrared (IR) images of the retina or a set of optical coherence tomography (OCT) images of the retina.

Step 240 includes generating, using the set of FAF images and the one or both of the set of IR images or the set of OCT images, a GA lesion segmentation mask including one or more GA lesion segments corresponding to the one or more GA lesions in the retina. In some embodiments, the generating includes generating the GA lesion segmentation mask using a neural network, the neural network including a U-Net deep learning neural network having an encoder and a decoder. In such cases, the process 200 may further comprise generating, using the encoder, an encoded image input by concatenating the set of FAF images and the one or both of the set of IR images or the set of OCT images. In some instances, the generating the GA lesion segmentation mask includes decoding the encoded image input using the decoder of the U-Net deep learning neural network.

In some embodiments, the generating includes generating the GA lesion segmentation mask using a neural network, the neural network including a Y-Net deep learning neural network having a first encoder, one or both of a second encoder or a third encoder, and a decoder. In such cases, the process 200 further comprises generating, via the first encoder and using the set of FAF images, an encoded FAF image input; and performing one or both of: generating, via the second encoder, encoded IR image input from the set of IR images; or generating, via the third encoder, encoded OCT image input from the set of OCT images. Further, in some instances, the process 200 comprises generating an encoded image input by concatenating the encoded FAF image input and one or both of the encoded IR image input or the encoded OCT image input; and the generating the GA lesion segmentation mask includes decoding the encoded image input using the decoder of the Y-Net deep learning neural network.

Some embodiments of process 200 further comprise extracting, by a processor, a feature of the one or more GA lesions in the retina from the GA lesion segmentation mask. Further, the process 200 may also comprise generating, by the processor, a recommendation for treating the one or more GA lesions based on the extracted feature. In some embodiments, the extracted feature includes a number of the one or more GA lesions.

Some embodiments of process 200 further comprise combining, by the processor, the one or more GA lesion segments into a single lesion component, the extracted feature including one or more of an area, a perimeter, a Feret diameter, or an excess rim intensity, of the single lesion component.

Figure 3A:
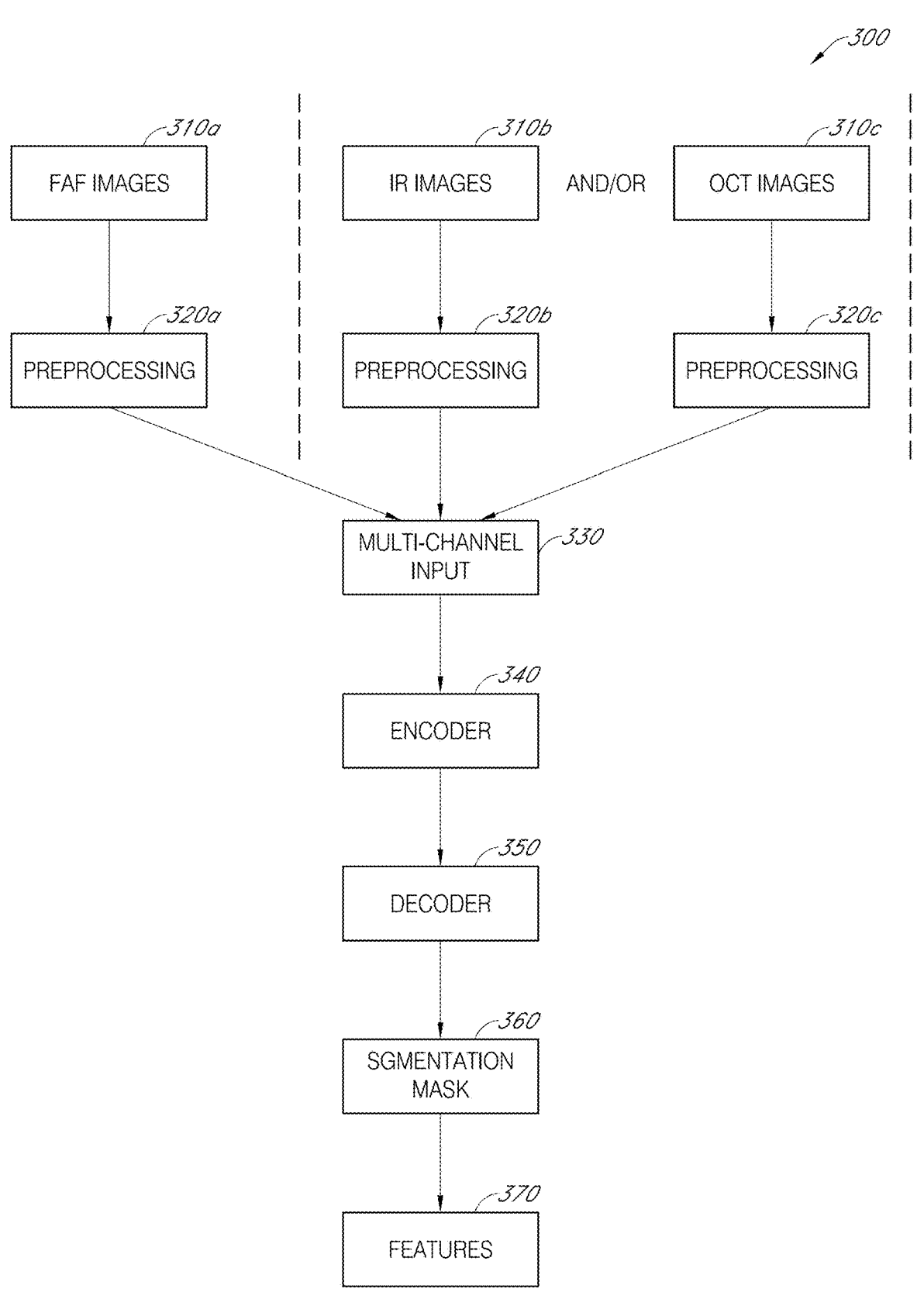
FIGS. 3A-3B illustrate a U-Net deep learning neural network, and use thereof, for evaluating a geographic atrophy lesion in accordance with various embodiments.

FIG. 3A illustrates a process 300 that utilizes a U-Net deep learning neural network to evaluate a geographic atrophy lesion in accordance with various embodiments. In some embodiments, the process 300 may use a multimodal approach where images of a retina having one or more GA lesions are obtained using multiple different imaging techniques for segmentation via the U-Net deep learning neural network (alternatively referred in shorthand as the "U-Net"). In some instances, the U-Net may receive, for example from a cSLO, a set of FAF images 310*a* of a retina of a retina having one or more GA lesions. The U-Net may also receive a set of IR images 310*b* (e.g., NIR images) of the retina from IR imaging device and/or a set of OCT images 310*c* (e.g., volume OCT images) of the retina from OCT imaging device.

In some embodiments, one or more of the received multimodal image inputs, i.e., one or more of the set of FAF images 310*a*, the set of IR images 310*b*, and the set of OCT images 310*c*, may be pre-processed 320*a*, 320*b*, 320*c* prior to being integrated as a multi-channel image input 330. For example, the image inputs may be resized or their intensities may be normalized (e.g., to a scale between 0 and 1). In the case of the set of OCT images 310*c*, the preprocessing 320*c* may include applying a histogram matching to the volume OCT images 310*c*, and flattening each B-scan along Bruch's membrane to generate en-face OCT images. In some cases, the en-face OCT images may then be combined to generate a multi-channel en-face OCT image input. For example, three en-face images or maps may be averaged over full depth, above Bruch's membrane, and sub-Bruch's membrane depths, may be combined to generate a three-channel en-face OCT image input. In some instances, the pre-processed set of multimodal image inputs may be integrated (e.g., concatenated) as a multi-channel image input 330, which may then be encoded by the encoder 340 of the U-Net.

An example architecture of the U-Net that may be used for segmenting retinal images as discussed in the present disclosure is presented below with reference to a multimodal image input including a set of FAF images and a set of NIR images. It is to be understood, however, that the example architecture and related discussion are for illustrative purposes and that the present disclosure is applicable to any U-Net architecture applied to multimodal image inputs including different number and types of sets of retinal images. In some embodiments, the U-Net architecture may be designed to predict and classify each pixel within an image (e.g., the multi-channel image input 330), which allows for more precise segmentation with fewer training images. In some instances, the U-Net may include a contractive encoder E 340 and an expansive decoder D 350. In this architecture, the pre-processed sets of images (e.g., the set of FAF images 310*a*, the set of IR images 310*b*, and the set of OCT images 310*c* after their respective pre-processing steps 320*a*, 320*b*, 320*c*) may be integrated or concatenated to generate the multi-channel input 330, which is then encoded with the contractive encoder E 340. In some instances, the encoded images may then be passed to the expansive decoder D 350 for generating the segmentation mask 360. The process, with reference to a multimodal image input including a FAF image 310*a* and a NIR image 310*b* as an example illustration, may be expressed as:

$$(Z, S) = E(concat(FAF, NIR));$$

$$P = D(Z, S),$$

wherein "FAF" stands for the FAF image, and "NIR" stands for the NIR image.

Figure 3B:
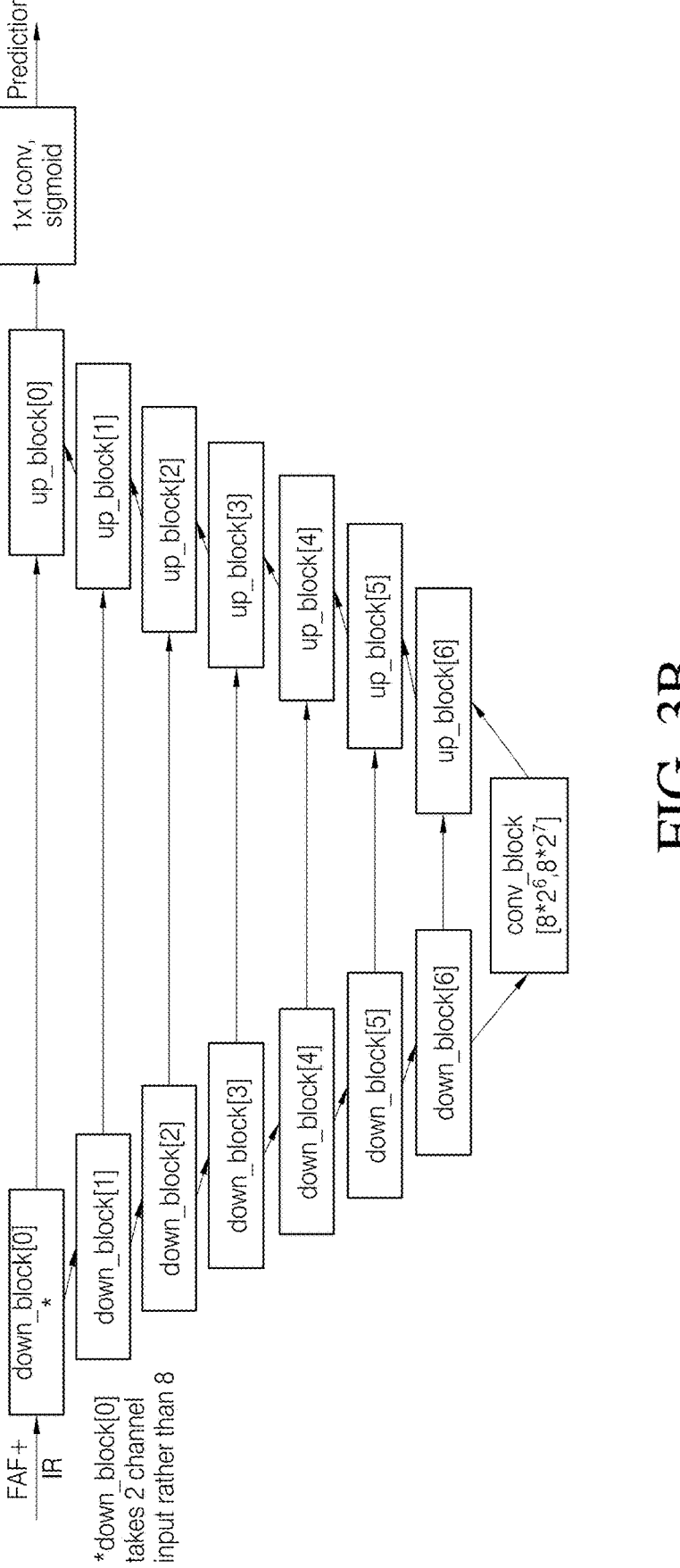

An example embodiment of the U-Net architecture is shown in FIG. 3B, where the contractive encoder E 340 alternates convolution blocks and downsampling operations, such that six downsamples can be performed in total. Each convolution block includes two 3×3 convolutions. Each convolution can be followed by a group normalization (GroupNorm) and rectified linear unit (ReLU) activation. The downsampling can be performed by a 2×2 maxpool operation. Z may be the final encoded image, and S can be the set of partial results of contractive encoder E 340 from before each downsampling step. In the decoder D 350, upsampling steps and convolution blocks may be alternated such that six upsamples can be performed in total. In some instances, the convolution blocks can be same or similar to those in the encoder, whereas the upsampling can be done by 2×2 transposed convolution. After each upsampling, the same-sized partial result from S may be copied in a skip connection and concatenated to the result. After the last convolution block, a 1×1 convolution can be performed followed by a sigma activation to yield a probability P between 0 and 1, from which the segmentation mask 360 may be generated. For example, the image pixels with a probability P at or greater than a threshold value may be assigned a value of "1" and identified as a GA lesion while the pixels with a probability P less than the threshold value are assigned a value of "0" indicating absence of a GA lesion, resulting in a binary segmentation map such as those shown in FIGS. 6A-6B.

In some embodiments, because of the encoder-decoder structure of the U-Net in FIG. 3B and the number and size of the convolution filters used, the U-Net deep learning neural network may learn image context information. In some instances, the upsampling in the decoder D 350 may help to propagate the image context information to the higher resolution channels. Image context information or features can be thought of as a mini-image—a small two-dimensional array of values. Features may match common aspects of the images. For example, in the case of image of letter 'X', features consisting of diagonal lines and a crossing may capture most or all the important characteristics of X. In some cases, these features may match up to any image of an X. As such, the features are essentially values of mini-images that capture some context information of the image. A large number of such features are generated by the U-Net architecture, which allow the U-Net deep learning neural network to learn the relationship between the image and the corresponding label/mask.

Returning to FIG. 3A, in some embodiments, features 370 of the one or more GA lesions of the retina may be extracted from the segmentation mask 360. For example, the number of the one or more GA lesions may be determined from the segmentation mask 360. Other features 370 that may be extracted or determined from the segmentation mask 360 include but are not limited to size, shape, area, perimeter, Feret diameter, circularity, excess rim intensity, and/or the like, of the GA lesions. In some instances, the one or more GA lesions may be fragmented, and in such cases, the above-noted features 370 may refer to the parameters of a single lesion component that is composed of the one or more GA lesions. That is, these parameters (i.e., size, shape, area, perimeter, Feret diameter, circularity, excess rim intensity, etc.) may be extracted or determined for a single lesion component that combines the one or more GA lesions. In some instances, a recommendation for treating the one or more GA lesions of the retina may be determined or generated based on the extracted features 370. For example, an ophthalmologist may diagnose the GA lesions (e.g., the stage or severity of the GA lesion) and prescribe a treatment based on the extracted features 370.

Figure 4A:
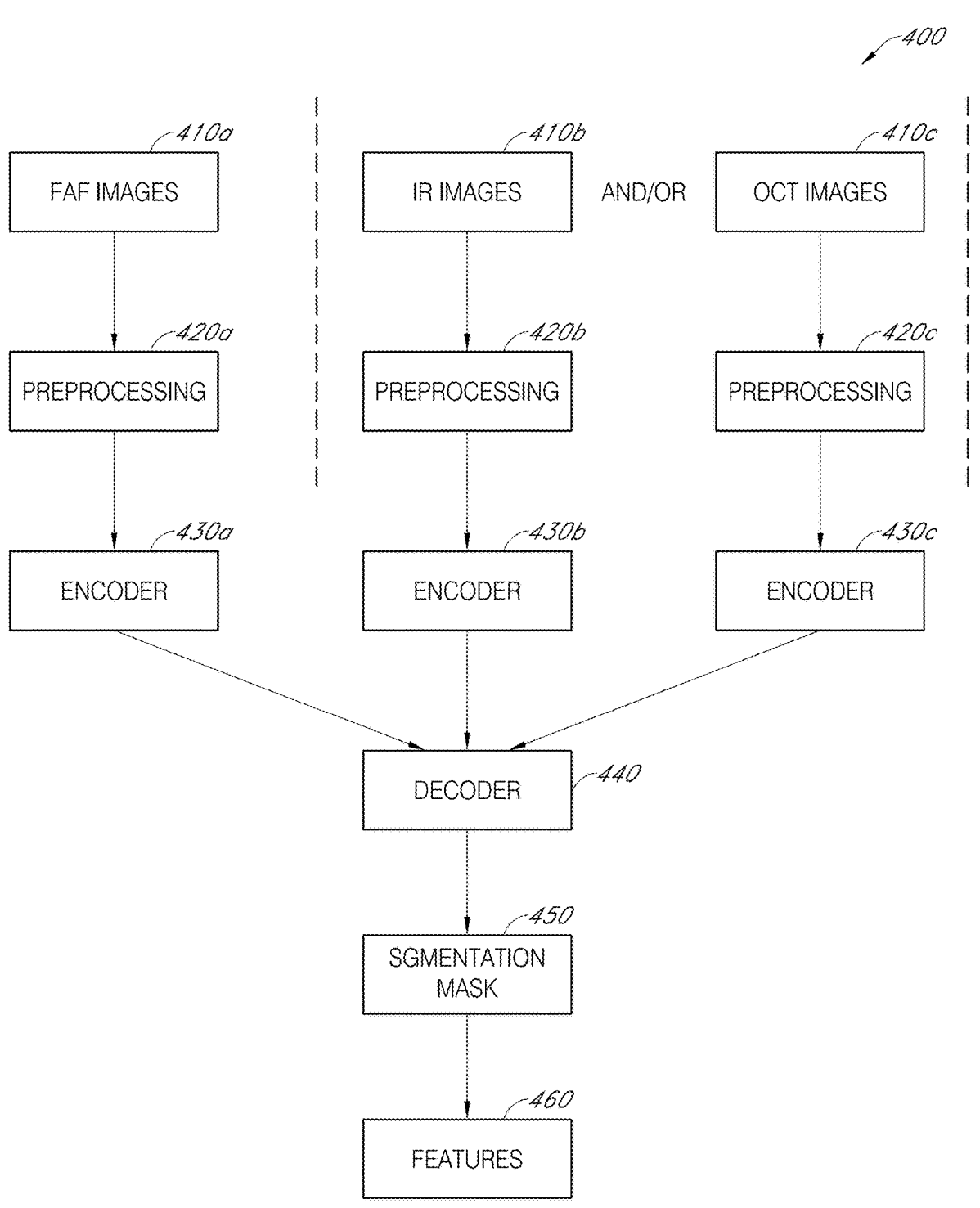
FIGS. 4A-4B illustrate a Y-Net deep learning neural network, and use thereof, for evaluating a geographic atrophy lesion in accordance with various embodiments.

FIG. 4A illustrates a process 400 that utilizes a Y-Net deep learning neural network to evaluate a geographic atrophy lesion in accordance with various embodiments. In some embodiments, the process 400 may use a multimodal approach where images of a retina having one or more GA lesions are obtained using multiple different imaging techniques for segmentation via the Y-Net deep learning neural network (alternatively referred to in shorthand as the "Y-Net"). In some instances, the Y-Net may receive, for example from a cSLO, a set of FAF images 410a of a retina of a retina having one or more GA lesions. The Y-Net may also receive a set of IR images 410b (e.g., NIR images) of the retina from an IR imaging device and/or a set of OCT images 410c (e.g., volume OCT images) of the retina from an OCT imaging device.

In some embodiments, one or more of the received multimodal image inputs, i.e., one or more of the set of FAF images 410a, the set of IR images 410b, and the set of OCT images 410c, may be pre-processed 420a, 420b, 420c prior to being encoded by respective encoders 430a, 430b, 430c of the Y-Net. For example, the image inputs may be resized or their intensities may be normalized (e.g., to a scale between 0 and 1). In the case of the set of OCT images 410c, the preprocessing 420c may include applying a histogram matching to the volume OCT images 410c, and flattening each B-scan along Bruch's membrane to generate en-face OCT images. In some cases, the en-face OCT images may then be combined to generate a multi-channel en-face OCT image input. For example, three en-face images or maps may be averaged over full depth, above Bruch's membrane, and sub-Bruch's membrane depths, may be combined a three-channel en-face OCT image input. In some instances, as noted above, the pre-processed set of multimodal image inputs (e.g., the set of FAF images 410a, the set of IR images 410b, and the set of en-face OCT images 410c) may be encoded by respective encoders 430a, 430b, 430c of the Y-Net.

In some instances, the Y-Net may have as many encoders as the number of modalities that are sources of the retinal images. For example, if the multimodal image input to the Y-Net includes a pair of sets of images of the retina (e.g., the pair including the set of FAF images 310a and the set of IR images 310b (but not the set of OCT images 310c, for instance), or the pair including the set of FAF images 310a and the set of OCT images 310c (but not the set of IR images 310b, for instance)), then the Y-Net may be configured to have two encoders where each encoder is configured to encode one of the pair of sets of images. As another example, if the multimodal image input to the Y-Net includes three sets of images of the retina (e.g., the set of FAF images 310a, the set of IR images 310b, and the set of en-face OCT images 310c), then the Y-Net may be configured to have three encoders (e.g., encoders 430a, 430b, 430c) where each encoder is configured to encode one of the three sets of images.

An example architecture of the Y-Net that may be used for segmenting retinal images as discussed in the present disclosure is presented below with reference to a multimodal image input including a set of FAF images and a set of NIR images. It is to be understood, however, that the example architecture and related discussion are for illustrative purposes and that the present disclosure is applicable to any Y-Net architecture applied to multimodal image inputs including different number and types of sets of retinal images. In some embodiments, the Y-Net may include as many encoder branches as the modalities of the image input (e.g., two encoders $E_1$ 430a, and $E_2$ 430b) and a decoder D 440. In this architecture, the pre-processed sets of images (e.g., the set of FAF images 410a, the set of IR images 410b, and the set of OCT images 410c after their respective pre-processing steps 420a, 420b, 420c) may be separately encoded with their respective encoders. For example, with reference to FIG. 4A, the set of FAF images 410a after pre-processing 420a and the set of IR images 410b after pre-processing 420b may be encoded separately by encoder $E_1$ 430a and encoder $E_2$ 430b, respectively, before being integrated or concatenated prior to decoding by the decoder D 440 of the Y-Net, from which the segmentation mask 450 may be generated. The process, with reference to a multi-modal image input including a FAF image 410a and a NIR image 410b as an example illustration, may be expressed as:

$$(Z_1, S_1) = E_1(FAF);$$

$$(Z_2, S_2) = E_2(NIR);$$

$$P = D(concat(Z_1, Z_2), S_1).$$

In some instances, the encoder $E_1$ 430a and encoder $E_2$ 430b may have same or similar architecture as the encoder 340 of the U-Net in FIGS. 3A-3B, except that the image inputs of encoder $E_1$ 430a and encoder $E_2$ 430b are single-channel image inputs, i.e., pre-processed set of FAF images 410 and set of NIR images 410b, respectively, while the image input of the encoder 340 is the multi-channel image input 330. Further, the decoder D 440 may have same or similar architecture as that of the decoder D 350, except that the input of the former may have as many channels as the number of image input modalities. For instance, when the multimodal image input includes a FAF image 410a and a NIR image 410b as in the above example illustration, the input of the decoder D 440 may have twice as many channels as that of the encoder 340. Further, in some instances, the partial results $S_1$ from the first encoder $E_1$ (e.g., FAF encoder $E_1$) were used in the decoder D 440, but not the partial results from the second encoder $E_2$ (e.g., NIR encoder $E_2$). The probability P, which has a value between 0 and 1, may then be calculated from the decoder D 440, from which the segmentation mask 450 may be generated as discussed above with reference to FIG. 3A. That is, the image pixels with a probability P at or greater than a threshold value may be assigned a value of "1" and identi-fied as a GA lesion while the pixels with a probability P less than the threshold value are assigned a value of "0" indi-cating absence of a GA lesion, resulting in a binary seg-mentation map such as those shown in FIGS. 6A-6B.

Figure 4B:
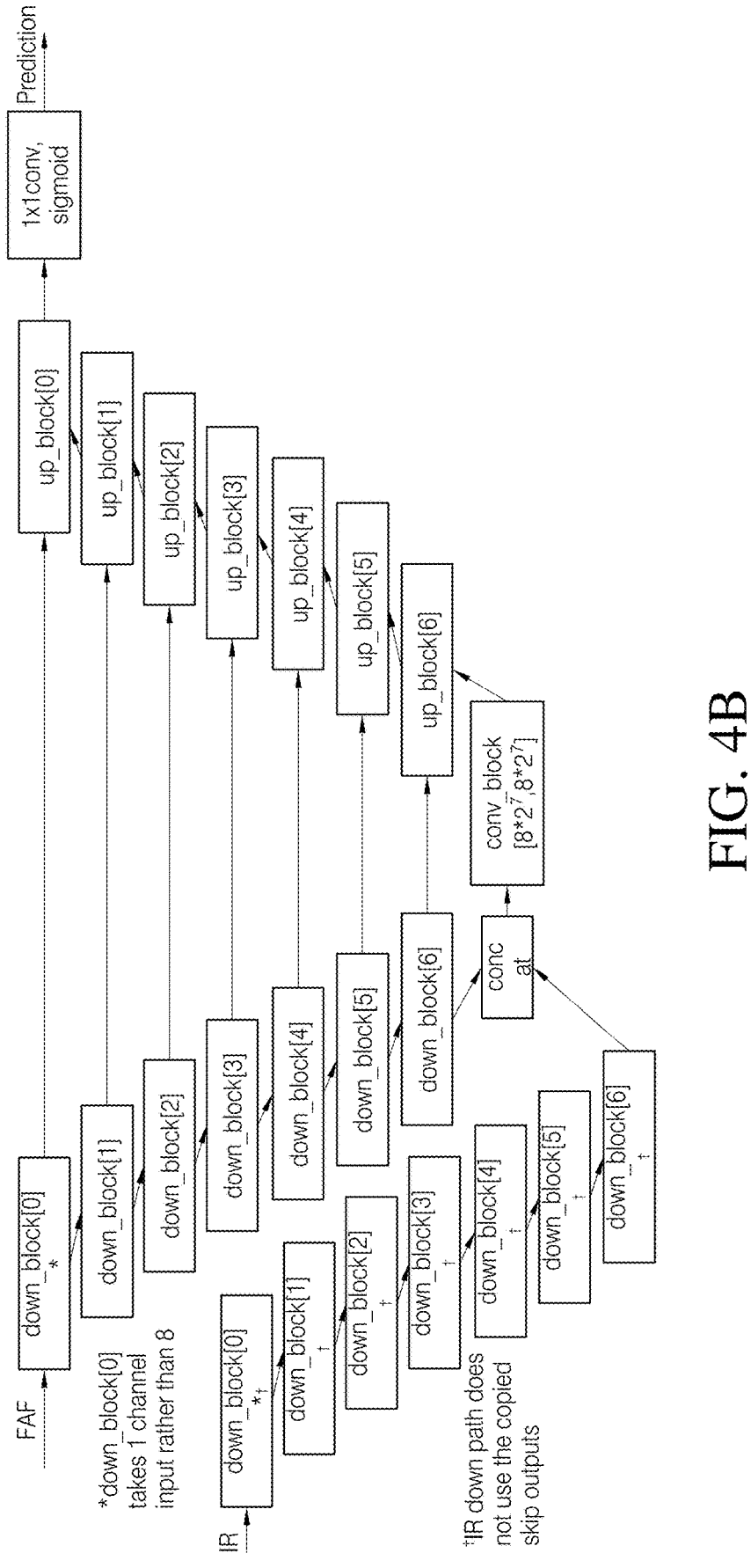

As discussed above with respect to the U-Net, the encoder-decoder structure of the Y-Net in FIG. 4B and the number and size of the convolution filters used, the Y-Net deep learning neural network may learn image context information. In some instances, the upsampling in the decoder D 440 may help to propagate the image context information to the higher resolution channels. Image context information or features can be thought of as a mini-im-age—a small two-dimensional array of values. Features may match common aspects of the images. For example, in the case of image of letter 'X', features consisting of diagonal lines and a crossing may capture most or all the important characteristics of X. In some cases, these features may match up to any image of an X. As such, the features are essentially values of mini-images that capture some context information of the image. A large number of such features are generated by the Y-Net architecture, which allow the Y-Net deep learning neural network to learn the relationship between the image and the corresponding label/mask.

In some embodiments, features 460 of the one or more GA lesions of the retina may also be extracted from the segmentation mask 450 as discussed above with reference to FIG. 3A. For example, the number, size, shape, area, perim-eter, Feret diameter, circularity, excess rim intensity, and/or the like, of the one or more GA lesions, may be determined from the segmentation mask 450. As noted above, if the one or more GA lesions are fragmented, the above-noted features 460 may refer to the parameters of a single lesion component that is composed of the one or more GA lesions. That is, these parameters (i.e., size, shape, area, perimeter, Feret diameter, circularity, excess rim intensity, etc.) may be extracted or determined for a single lesion component that combines the one or more GA lesions. In addition, in some instances, a recommendation for treating the one or more GA lesions of the retina may be determined or generated based on the extracted features 460. For example, an oph-thalmologist may diagnose the one or more GA lesions and prescribe a treatment based on the extracted features 460 (e.g., based on the size of the GA lesions).

In some embodiments, the U-Net deep learning neural network of FIGS. 3A-3B and/or the Y-Net deep learning neural network of FIGS. 4A-4B may be trained to generate the segmentation mask 360 and 450, respectively, as fol-lows. In some instances, the U-Net architecture and the Y-Net architecture may be initialized with random weights. The loss function to be minimized can be the Dice loss, defined as 1 minus the Dice coefficient. Adam optimizer, an algorithm for first-order gradient-based optimization of sto-chastic objective functions, may be used for training. An initial learning rate may be set to $1e^{-3}$ (i.e., 0.001) and multiplied by 0.1 every 30 epochs for 100 epochs without early stopping. The validation dataset may then be used to tune and select the hyperparameters. Once the hyperparam-eters are selected, in some embodiments, the U-Net and the Y-Net may be used to predict the GA lesion segmentation masks on the test set. To assess the longitudinal perfor-mance, GA lesion enlargement may be computed as absolute change (in $mm^2$) in GA lesion area over time, for example, from baseline to month 6, and baseline to month 12, in the test set. Further, GA lesion enlargements of U-Net and/or Y-Net predicted segmentations can be compared with those of grader annotations. Dice scores may also be calculated and reported as the performance metric on CNN segmenta-tions. Further, Pearson correlation coefficient (r) may be used to assess the longitudinal performance.

In some embodiments, during training of the neural networks, a modified version of the ground truth masks can be used to weight the edges of the lesions more than the interiors. For example, the modified masks may be defined as follows:

$$dt\_mask \leftarrow edt(orig\_mask)$$

$$normalized\_edt\_mask \leftarrow min(edt\_mask/max(edt\_mask), 0.5)$$

$$modified_{mask} \leftarrow orig_{mask} * (1 - normalized_{edt_{mask}}),$$

where orig_mask denotes the original ground truth mask with values 0 and 1, and edt denotes the Euclidean distance transform. In some instances, all operations other than edt and max may be elementwise operations, where max returned the maximum value of the input array. The result was a mask that was 0 where there was no lesion, and at least 0.5 where there was a lesion. In some cases, higher values (up to 1) may be recorded near the edges of the lesion.

In some instances, the Dice function, expressed as fol-lows, may be used:

$$Dice = \frac{2 * sum(pred * modified\_mask) + \varepsilon}{sum(pred) + sum(modified\_mask) + \varepsilon},$$

where ε is a parameter used to ensure smoothness when the masks are empty (e.g., ε=1). The gradient of the Dice function with this modification may aid the neural networks (U-Net or Y-Net) to output the correct probability value P between 0 and 1 (i.e., the correct segmentation masks). In other words, the neural networks may be aided by the gradient of the Dice function to compute an increased probability value P (e.g., up to a value of 1) for regions or pixels on the input images where there is a GA lesion and decreased probability P (e.g., down to a value of 0) for regions or pixels where there are no GA lesions. In some instances, the neural networks may put increased emphasis on the borders of the GA lesions, rather than the interior, which may be suitable because the neural networks may find the interior of the GA lesion easier to properly identify, and as such the neural networks may expend less into learning to do so.

In some embodiments, during validation and testing, the original mask can be used, and the prediction or probability may have a value of 1 when the predicted probability was greater than a threshold, and 0 otherwise. For example, when the prediction or probability is equal to or greater than the threshold 0.5, the probability P may be assigned a value of 1 indicating the presence of a GA lesion, while when the prediction or probability is less than the threshold 0.5, the probability P may be assigned a value of 0 indicating the absence of a GA lesion.

IV. Example Application of the Systems and Methods Disclosed Herein

Figure 5:
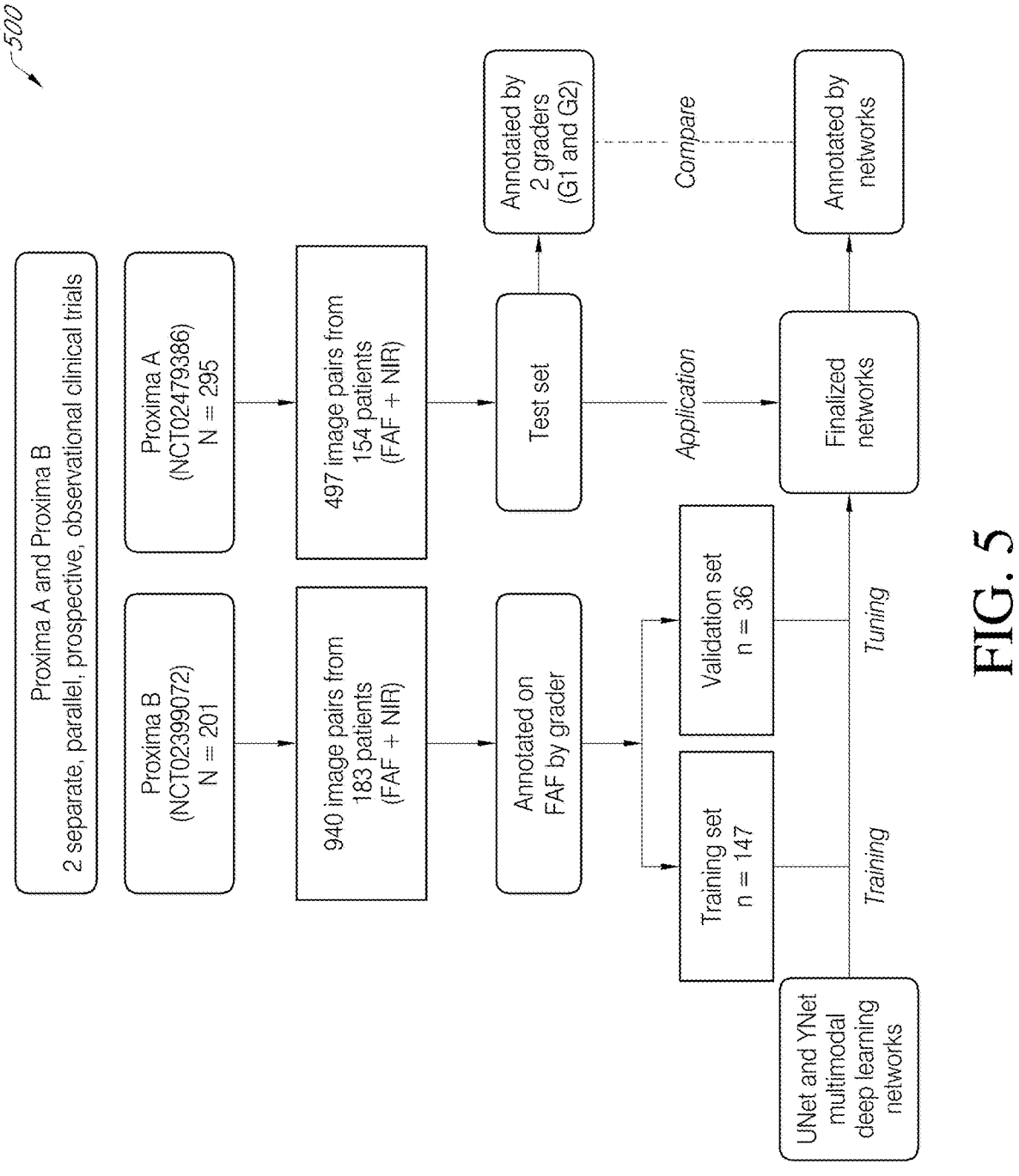
FIG. 5 illustrates example workflow for segmenting FAF images and NIR images using Y-Net and U-net deep learning neural networks in accordance with various embodiments.

FIG. 5 illustrates example workflow 500 for a retrospective study segmenting FAF images and NIR images using Y-Net and U-net deep learning neural networks in accordance with various embodiments. The study was performed using FAF and NIR imaging data from study eyes of patients enrolled in the observational clinical studies titled "Study of Disease Progression in Participants with Geographic Atrophy Secondary to Age-Related Macular Degeneration" (so-called Proxima A and Proxima B natural history studies of patients with GA). Proxima A patients had bilateral GA without choroidal neovascularization (CNV) at baseline and Proxima B patients had unilateral GA with or without CNV in the fellow eye at baseline.

FAF images at screening and follow-up visits were graded by two junior graders; when the junior graders disagreed, a senior adjudicator also graded the scans. Only scans graded by both junior graders were used for the results shown in FIGS. 6-11 (one patient was not included because of incomplete grading from the second grader). FAF images from Proxima B study were graded by a senior grader. As shown in FIG. 5, 940 FAF and NIR image pairs from 183 patients in Proxima B study were taken, lesions were annotated on the FAF images by a human grader, and the data was split at the patient level into the training set (images from 147 patients) with a total of 748 visits and the validation set (images from 36 patients) with a total of 192 visits. 90 FAF and NIR image pairs from 90 patients were used for testing. Patient visits without both FAF and NIR images were excluded. The U-Net and the Y-Net neural networks were trained as discussed above using the training set, and validated using the validation set.

In both studies, GA diagnosis and lesion area measurements were based on FAF imaging, where a minimum lesion diameter is used as a cutoff for a GA lesion to be recognized as one. In Proxima A, a GA lesion is recognized as one when the study eye has had a well-demarcated area of GA secondary to AMD with no evidence of prior or active CNV, total GA lesion size greater than 2.54 mm$^2$ but less than or equal to 17.78 mm$^2$ residing completely within the FAF imaging field (field 2-30°, image centered on the fovea), with perilesional banded or diffuse hyperautofluorescence patterns. If GA lesion was multifocal, the GA lesion is recognized as one when at least one focal lesion has an area greater than or equal to 1.27 mm$^2$. In Proxima B, a GA lesion is recognized as one when study eyes of patients with GA and without CNV, and CNV with or without GA in the fellow eye have a total lesion size between 1.27 mm$^2$ and 17.78 mm$^2$. In patients with unilateral GA and no CNV in the study eye, a GA lesion is recognized as one when its total lesion size is between 0.3 mm$^2$ and 17.78 mm$^2$ or, if multifocal, when at least one focal lesion has an area greater than or equal to 0.3 mm$^2$.

GA lesion sizes were derived from the GA lesions annotated by human graders (i.e., considered to be the ground truth) using RegionFinder software. Minimal size for individual lesions was set as 0.05 mm$^2$, which corresponds to about 175 μm diameter. The FAF and NIR images in the test set from Proxima A study were segmented using the U-Net and the Y-Net as discussed above with reference to FIGS. 3 and 4, respectively, and outputs from these neural networks were then compared with the ground truth (i.e., the annotations from the two graders G1 and G2). Corresponding infrared images were used for identification of small atrophic areas and atrophy delineation around the central fovea. Images and masks were resized to 768×768 pixels, and no normalization was performed.

FIGS. 6-11 show various measurement results extracted from the human grader-annotated and U-Net/Y-Net neural network-generated GA lesion segmentation masks obtained from the FAF and NIR images of the Proxima A study. FIGS. 6A-6B illustrate example segmentation results of FAF images and NIR images of a retina with GA lesions using two human graders G1 and G2 as well as Y-Net and U-net deep learning neural networks in accordance with various embodiments. In particular, in both FIG. 6A and FIG. 6B, the first rows show FAF image and NIR image of a retina at screening time, along with the GA lesion segmentation results performed by each human grader and neural network, and the Dice scores measuring the similarities of the segmentations performed by the graders and the neural networks (shown in more detail in FIG. 7). The second rows show the corresponding results for FAF image and NIR image of the same retina taken twelve months later.

FIG. 6A shows good agreement between the segmentation results of the human graders and the neural networks, confirmed by the rather high Dice scores, while FIG. 6B shows poorer agreement, which again is confirmed by the lower Dice scores. The poorer agreement shown in FIG. 6B may be related to foveal assessment, with the U-Net neural network and the Y-Net neural network identifying the fovea as a lesion. The Y-Net neural network seems to perform better than the U-Net neural network at avoiding segmenting the fovea; however, the differences and any fovea-specific advantage of the Y-Net may be minor. Poor agreement may also be due to the neural networks misinterpreting shadows as lesions or due to poor FAF image quality. It is to be noted that although correlation of lesion area is high, the contours are not identical.

Figure 7:
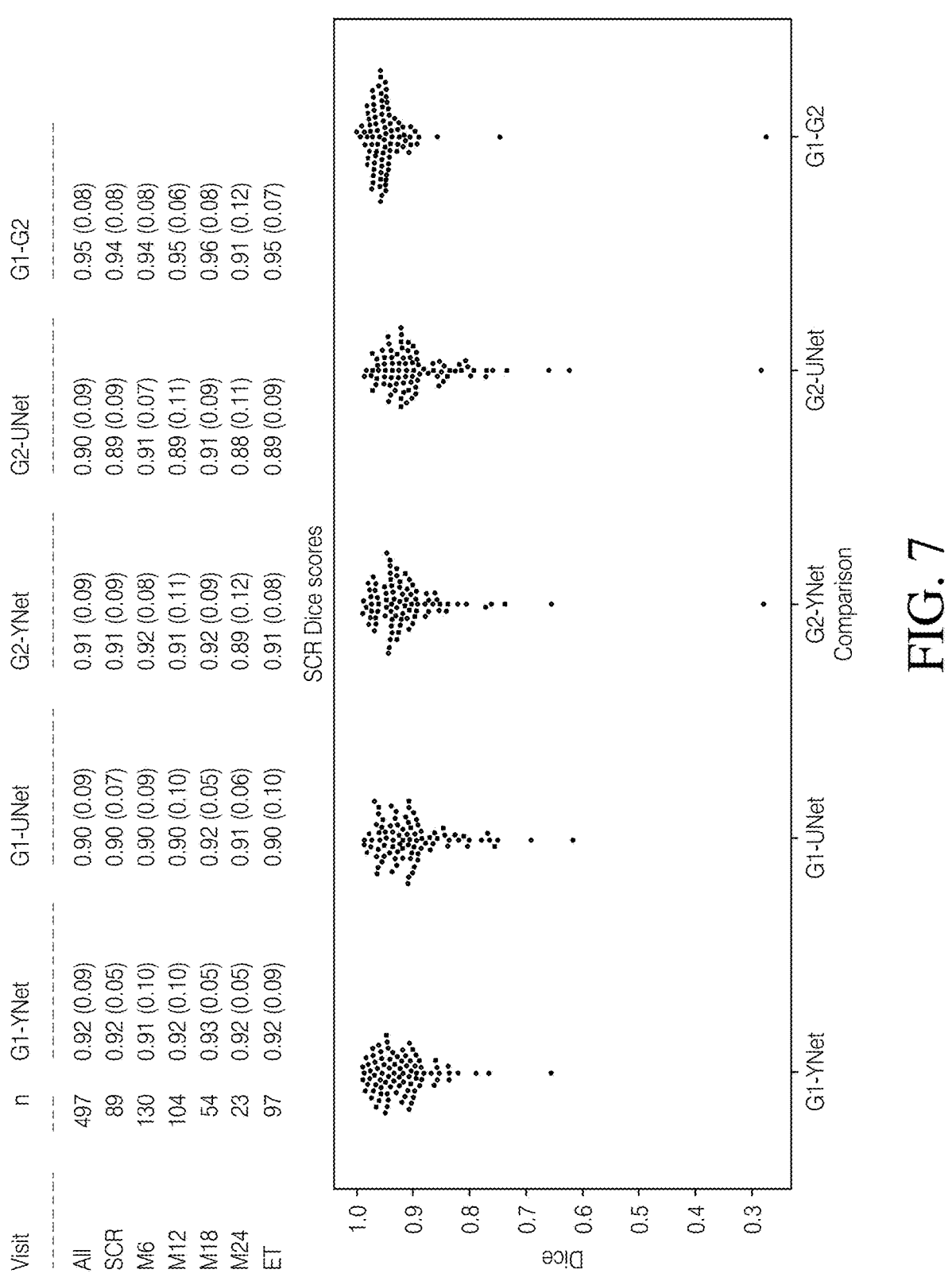
FIG. 7 shows example Dice similarity coefficient scores measuring similarities between segmentations performed by the Y-Net deep learning neural network, the U-Net deep learning neural network, and human graders in accordance with various embodiments.

FIG. 7 shows example Dice similarity coefficient scores measuring similarities between segmentations performed by the Y-Net deep learning neural network, the U-Net deep learning neural network, and human graders in accordance with various embodiments. In particular, FIG. 7 shows a table including Dice scores measuring the similarities between GA lesion segmentations performed by the first grader G1 and the Y-Net ("G1-YNet"), by the first grader G1 and the Y-Net ("G1-UNet"), by the second grader G2 and the Y-Net ("G1-YNet"), by the second grader G2 and the U-Net ("G1-UNet"), and by the first grader G1 and the second grader G2 ("G1-G2"), at the initial screening time ("SCR"), six months after screening ("M6"), twelve months after screening ("M12"), eighteen months after screening ("M18"), twenty four months after screening ("M24"), ("ET"), and combination thereof ("All"). Further, FIG. 7 shows a swarmplot including the afore-mentioned Dice scores at screening time. The results shown in the figure indicate that the agreement between the GA lesion segmentations performed by the neural networks and the human graders was similar to the agreement between the GA lesion segmentations performed by the two graders.

Figure 8A:
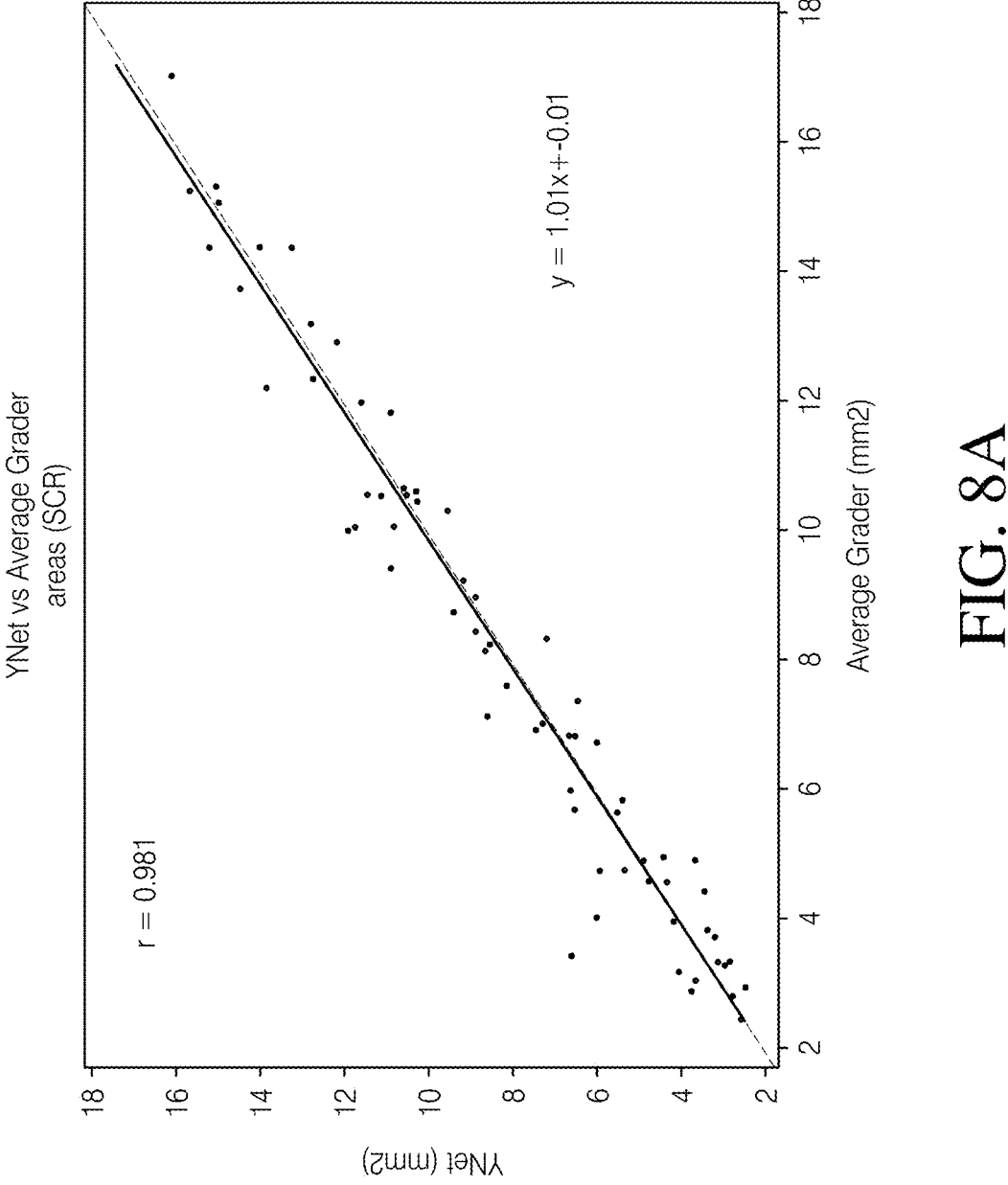
FIGS. 8A-8D show example comparisons of lesion area sizes at screening time as measured by the Y-Net deep learning neural network, the U-Net deep learning neural network, and human graders in accordance with various embodiments.
Figure 8B:
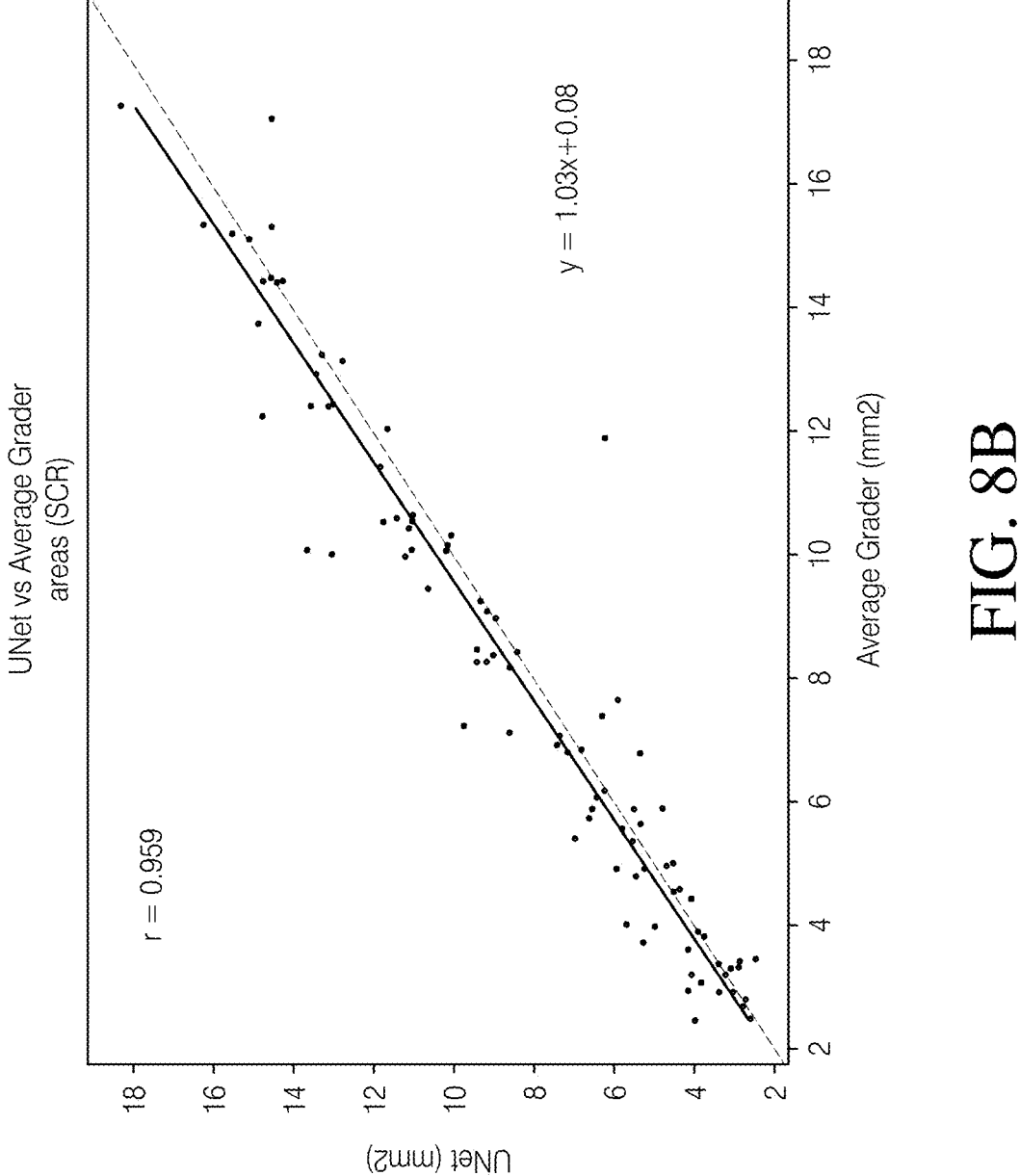
Figure 8C:
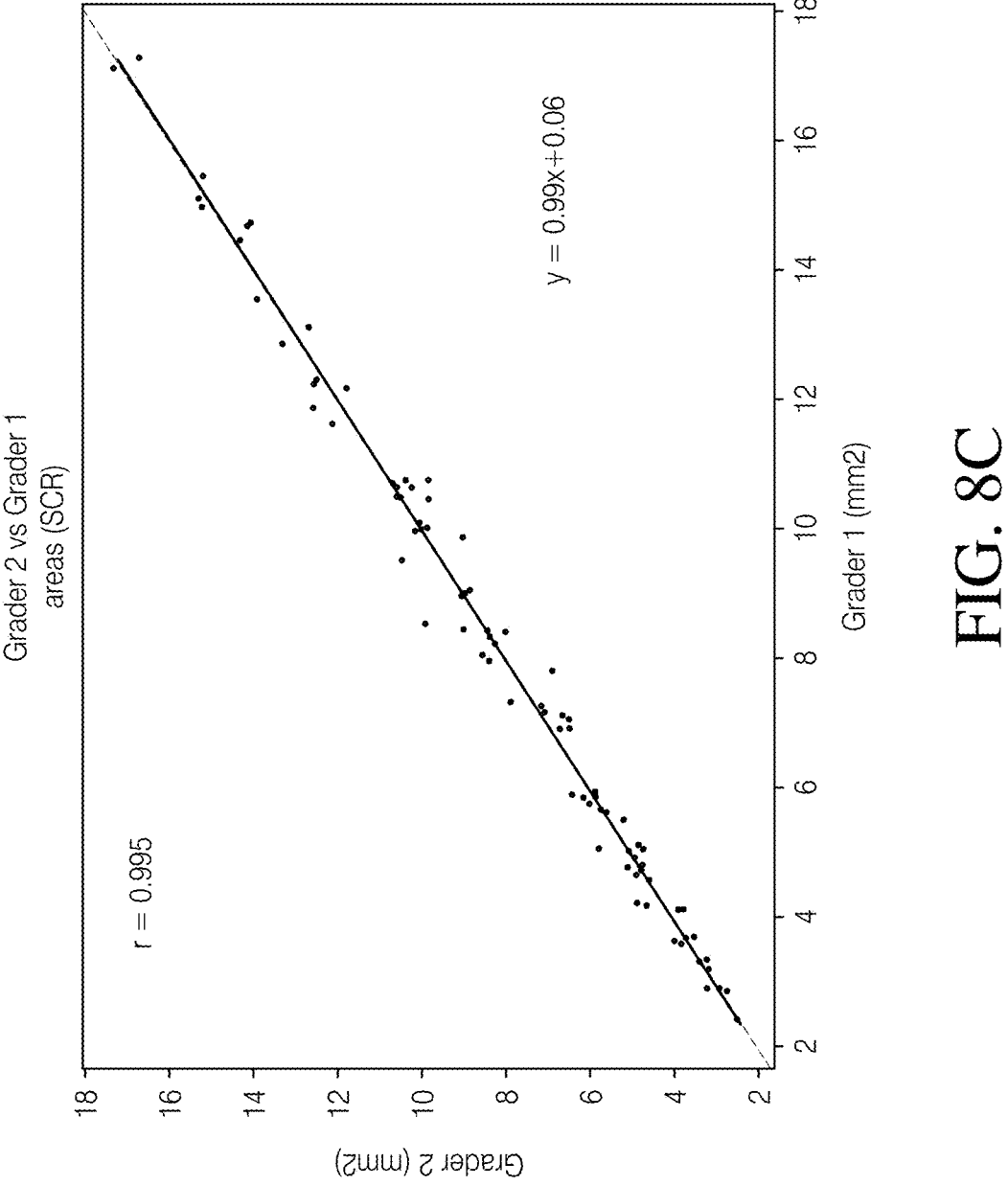
Figure 8D:
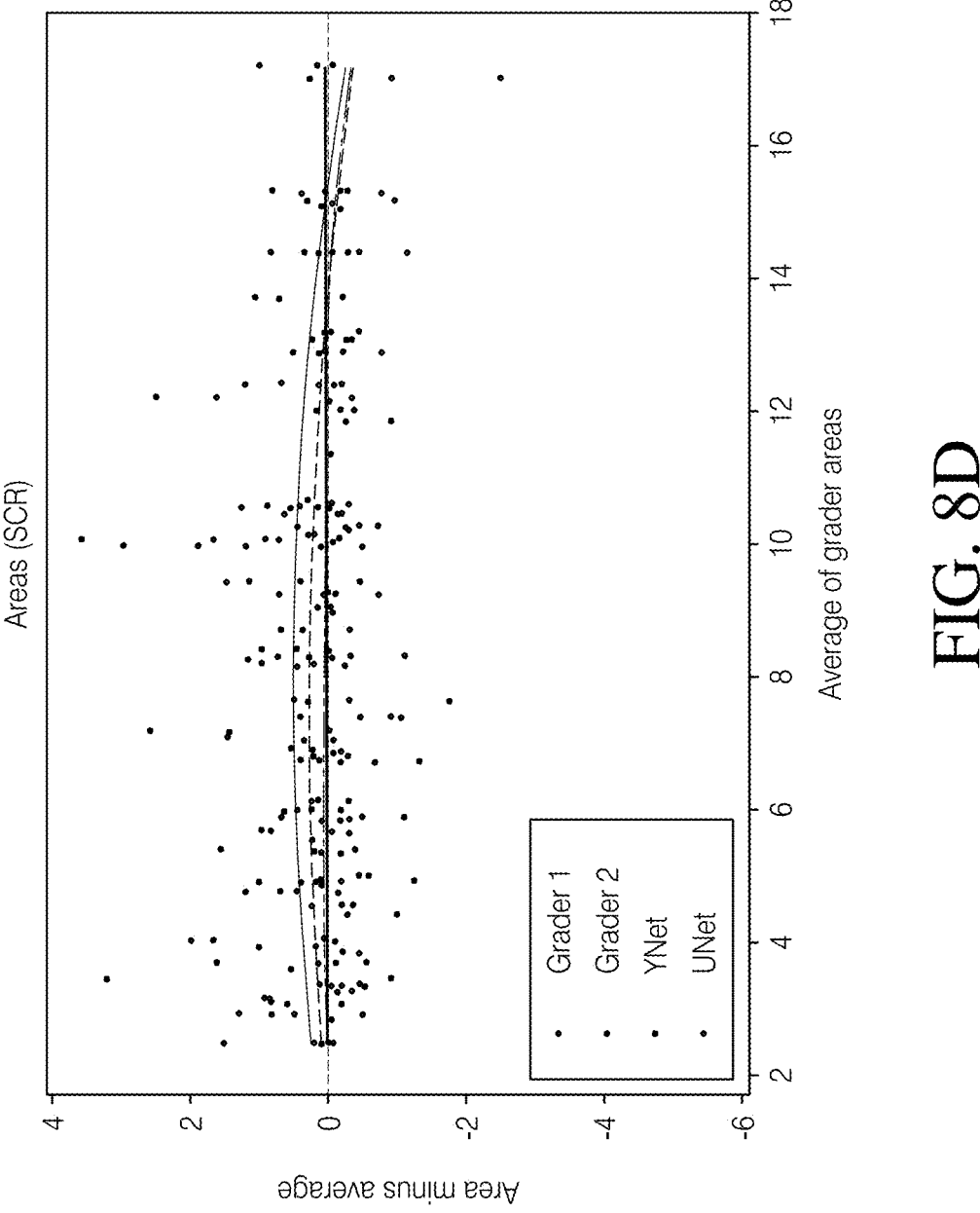

FIGS. 8A-8D show example comparisons of GA lesion area sizes at screening time as measured by the Y-Net deep learning neural network, the U-Net deep learning neural network, and human graders in accordance with various embodiments. In some embodiments, to assess the performance of the neural networks on individual GA lesion areas, correspondence of the areas of the GA lesions in the segmentation masks generated by the neural networks were compared with the average of the GA lesion areas of the segmentation masks annotated by the graders. FIG. 8A and FIG. 8B both show good agreement between the GA lesions areas at screening time in the segmentation masks generated by the Y-Net and the U-Net, respectively, and the average of the GA lesion areas of the segmentation masks annotated by the graders ("Average Grader"). FIG. 8C also shows good agreement between GA lesion areas at screening time in the segmentation masks annotated by the two graders. FIG. 8D shows a Bland-Altman plot, i.e., a difference plot, showing the difference between the GA lesion areas in the segmentation masks annotated by the graders and generated by the neural networks and the average of the GA lesion areas (the y-axis) as a function of the average (the x-axis). The figure also shows a smoothing degree 2 polynomial line to show the general trend. It should however be noted that, there can be an inherent statistical bias in these plots because the grader average is used as the baseline, hence the graders were a priori closer to the baseline than the neural networks.

Figure 9A:
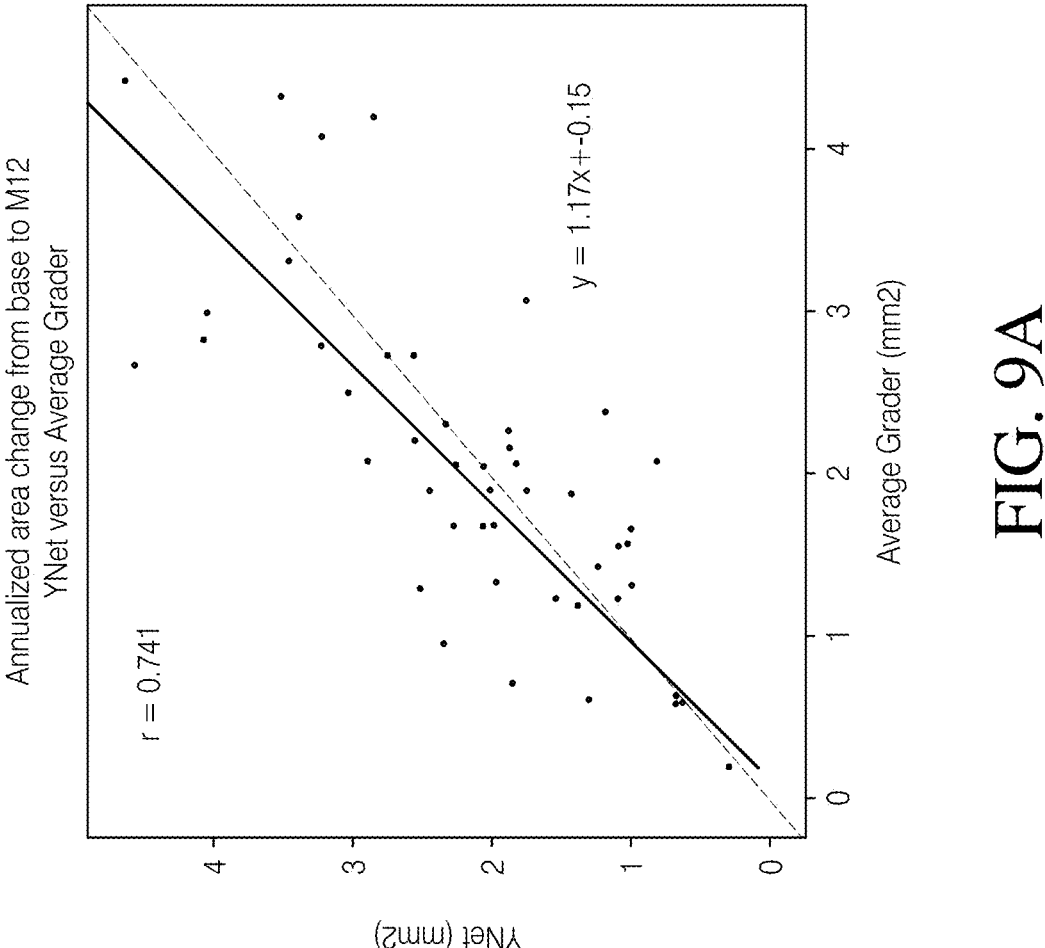
FIGS. 9A-9E show example comparisons of lesion area sizes at month 12 measured by the Y-Net deep learning neural network, the U-Net deep learning neural network, and human graders in accordance with various embodiments.
Figure 9B:
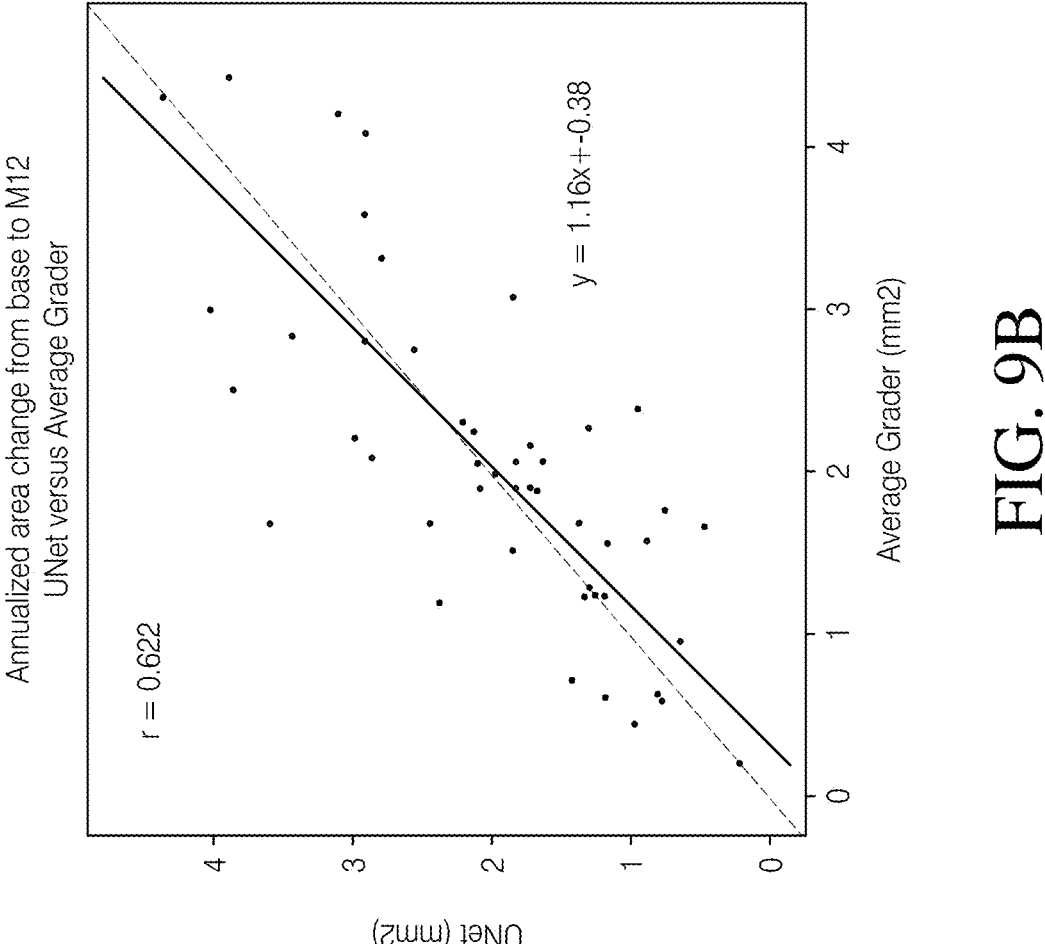
Figure 9C:
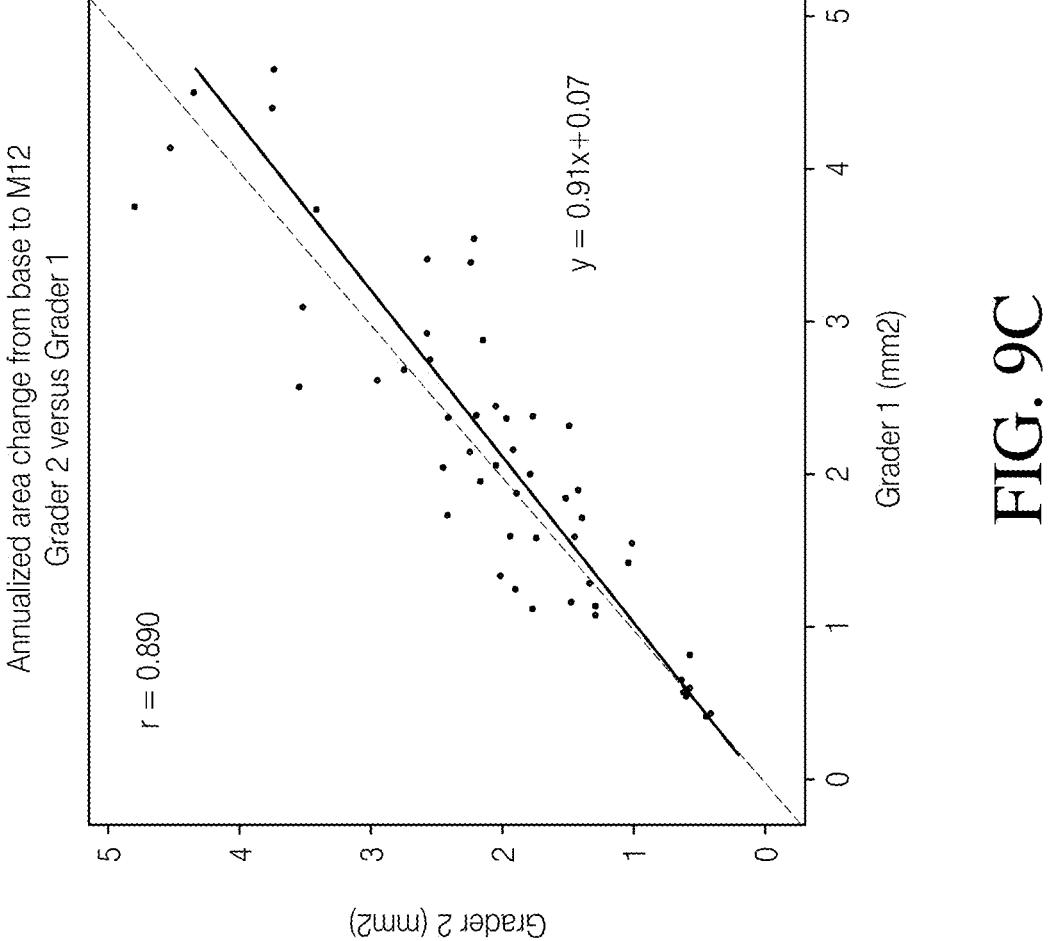
Figure 9D:
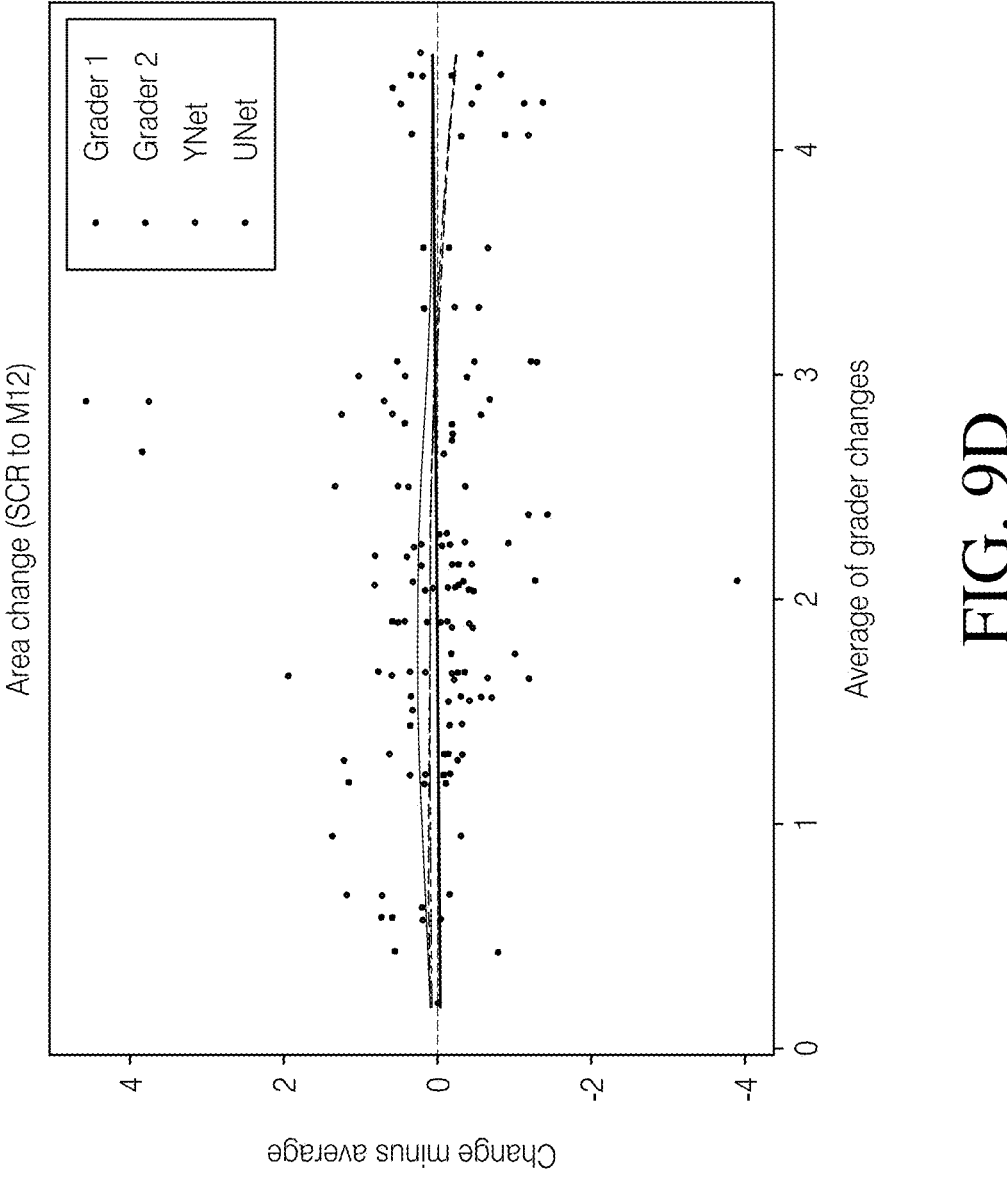
Figure 9E:
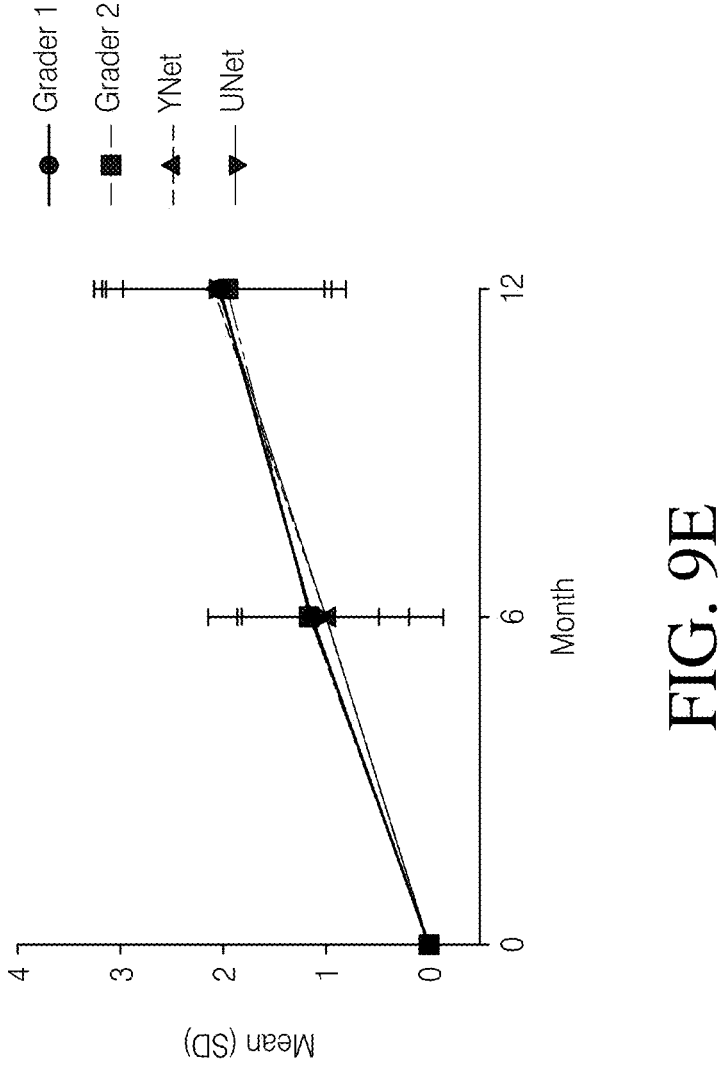

FIGS. 9A-9E show example comparisons of lesion area sizes at month 12 measured by the Y-Net deep learning neural network, the U-Net deep learning neural network, and human graders in accordance with various embodiments. In some embodiments, the neural network's capability to measure GA lesion area changes may be tested by measuring the GA lesion area of the same eye or retina at different time points. FIGS. 9A-9C show annualized GA lesion area changes (i.e., longitudinal area changes) from screening time to 12 months later between segmentations performed by the Y-Net and the "average grader" (FIG. 9A), between segmentations performed by the U-Net and the "average grader" (FIG. 9B), and between segmentations performed by the two graders (FIG. 9C). FIG. 9D shows a Bland-Altman plot showing the difference between the longitudinal changes in the GA lesion areas in the segmentation masks annotated by the graders and generated by the neural networks and the average of the GA lesion area changes (the y-axis) as a function of the average (the x-axis). The figure also shows a smoothing degree 2 polynomial line to show the general trend. FIGS. 9A-9D show that neural network-grader comparative results for longitudinal GA lesion areas are poor in comparison to the cross-sectional results (such as those shown in FIGS. 8A-8D). This poor performance over longitudinal measurements could potentially be a statistical artefact owing to the small magnitude of average change. In addition, the neural networks may not have the opportunity to compare against previous visit and treat each image independently. Comparison of screening to month 6 were also found to be generally even worse, potentially due to noise amplification and algorithmic error, as well as the small sample size. However, the comparison of measured area changes over time, shown in FIG. 9E, demonstrate similar mean change and CV between networks and graders, suggesting that although correlation is not high at the individual patient level or over short time windows, the neural networks perform well over time in measuring endpoints.

V. Artificial Neural Networks

Figure 10:
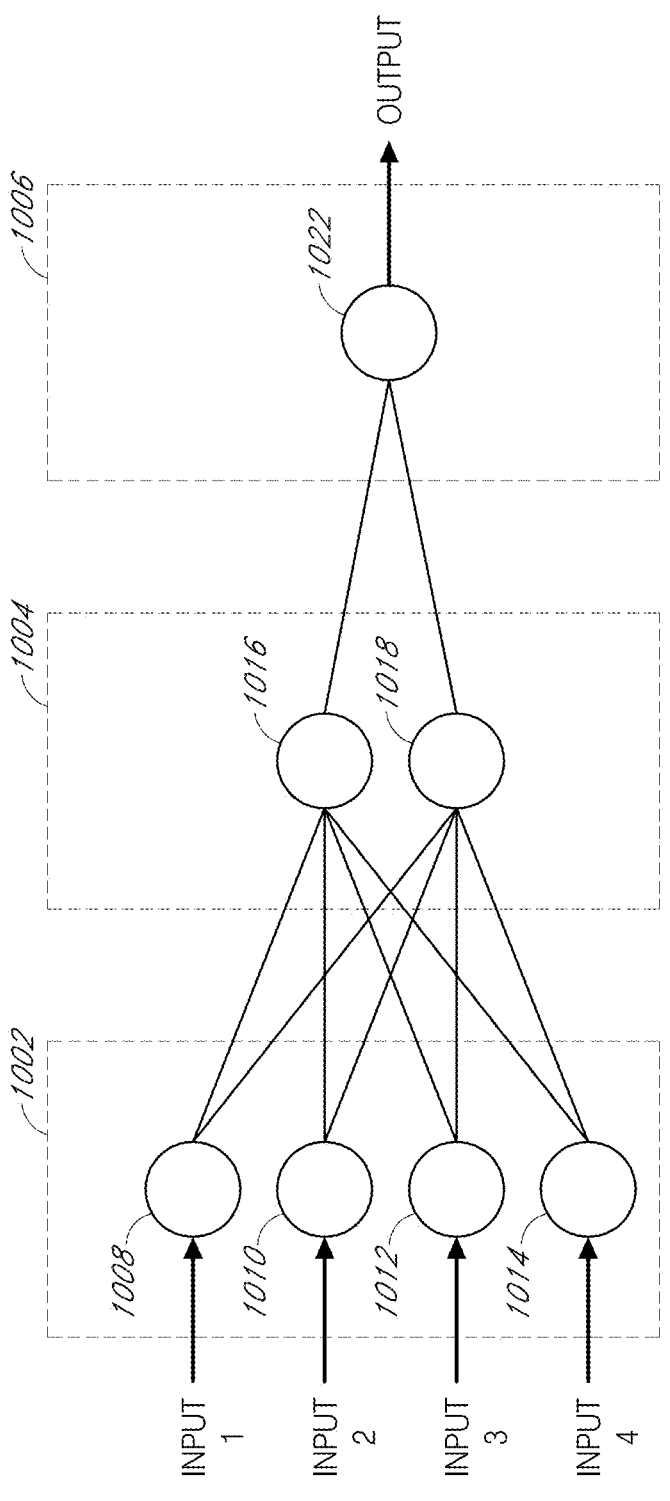
FIG. 10 illustrates an example neural network that can be used to implement the Y-Net deep learning neural network and the U-Net deep learning neural network in accordance with various embodiments.

FIG. 10 illustrates an example neural network that can be used to implement a computer-based model according to various embodiments of the present disclosure. For example, the neural network 1000 may be used to implement the lesion quantification system 114 of the lesion evaluation system 100. As shown, the artificial neural network 1000 includes three layers—an input layer 1002, a hidden layer 1004, and an output layer 1006. Each of the layers 1002, 1004, and 1006 may include one or more nodes. For example, the input layer 1002 includes nodes 1008-1014, the hidden layer 1004 includes nodes 1016-1018, and the output layer 1006 includes a node 1022. In this example, each node in a layer is connected to every node in an adjacent layer. For example, the node 1008 in the input layer 1002 is connected to both of the nodes 1016, 1018 in the hidden layer 1004. Similarly, the node 1016 in the hidden layer is connected to all of the nodes 1008-1014 in the input layer 1002 and the node 1022 in the output layer 1006. Although only one hidden layer is shown for the artificial neural network 1000, it has been contemplated that the artificial neural network 1000 used to implement the lesion quantification system 114 of the lesion evaluation system 100 may include as many hidden layers as necessary or desired.

In this example, the artificial neural network 1000 receives a set of input values and produces an output value. Each node in the input layer 1002 may correspond to a distinct input value. For example, when the artificial neural network 1000 is used to implement the lesion quantification system 114 of the lesion evaluation system 100, each node in the input layer 1002 may correspond to a distinct attribute of a set of FAF images 110, a set of IR images 112, or a set of OCT images 124.

In some embodiments, each of the nodes 1016-1018 in the hidden layer 1004 generates a representation, which may include a mathematical computation (or algorithm) that produces a value based on the input values received from the nodes 1008-1014. The mathematical computation may include assigning different weights to each of the data values received from the nodes 1008-1014. The nodes 1016 and 1018 may include different algorithms and/or different weights assigned to the data variables from the nodes 1008-1014 such that each of the nodes 1016-1018 may produce a different value based on the same input values received from the nodes 1008-1014. In some embodiments, the weights that are initially assigned to the features (or input values) for each of the nodes 1016-1018 may be randomly generated (e.g., using a computer randomizer). The values generated by the nodes 1016 and 1018 may be used by the node 1022 in the output layer 1006 to produce an output value for the artificial neural network 1000. When the artificial neural network 1000 is used to implement the lesion quantification system 114 of the lesion evaluation system 100, the output value produced by the artificial neural network 1000 may include a segmentation output 116.

The artificial neural network 1000 may be trained by using training data. For example, the training data herein may be a set of FAF images, a set of IR images, or a set of OCT images. By providing training data to the artificial neural network 1000, the nodes 1016-1018 in the hidden layer 1004 may be trained (adjusted) such that an optimal output is produced in the output layer 1006 based on the training data. By continuously providing different sets of training data, and penalizing the artificial neural network 1000 when the output of the artificial neural network 1000 is incorrect (e.g., when generating segmentation masks including incorrect GA lesion segments), the artificial neural network 1000 (and specifically, the representations of the nodes in the hidden layer 1004) may be trained (adjusted) to improve its performance in data classification. Adjusting the artificial neural network 1000 may include adjusting the weights associated with each node in the hidden layer 1004.

Although the above discussions pertain to an artificial neural network as an example of machine learning, it is understood that other types of machine learning methods may also be suitable to implement the various aspects of the present disclosure. For example, support vector machines (SVMs) may be used to implement machine learning. SVMs are a set of related supervised learning methods used for classification and regression. A SVM training algorithm—which may be a non-probabilistic binary linear classifier—may build a model that predicts whether a new example falls into one category or another. As another example, Bayesian networks may be used to implement machine learning. A Bayesian network is an acyclic probabilistic graphical model that represents a set of random variables and their conditional independence with a directed acyclic graph (DAG). The Bayesian network could present the probabilistic relationship between one variable and another variable. Another example is a machine learning engine that employs a decision tree learning model to conduct the machine learning process. In some instances, decision tree learning models may include classification tree models, as well as regression tree models. In some embodiments, the machine learning engine employs a Gradient Boosting Machine (GBM) model (e.g., XGBoost) as a regression tree model. Other machine learning techniques may be used to implement the machine learning engine, for example via Random Forest or Deep Neural Networks. Other types of machine learning algorithms are not discussed in detail herein for reasons of simplicity and it is understood that the present disclosure is not limited to a particular type of machine learning.

VI. Computer Implemented System

Figure 11:
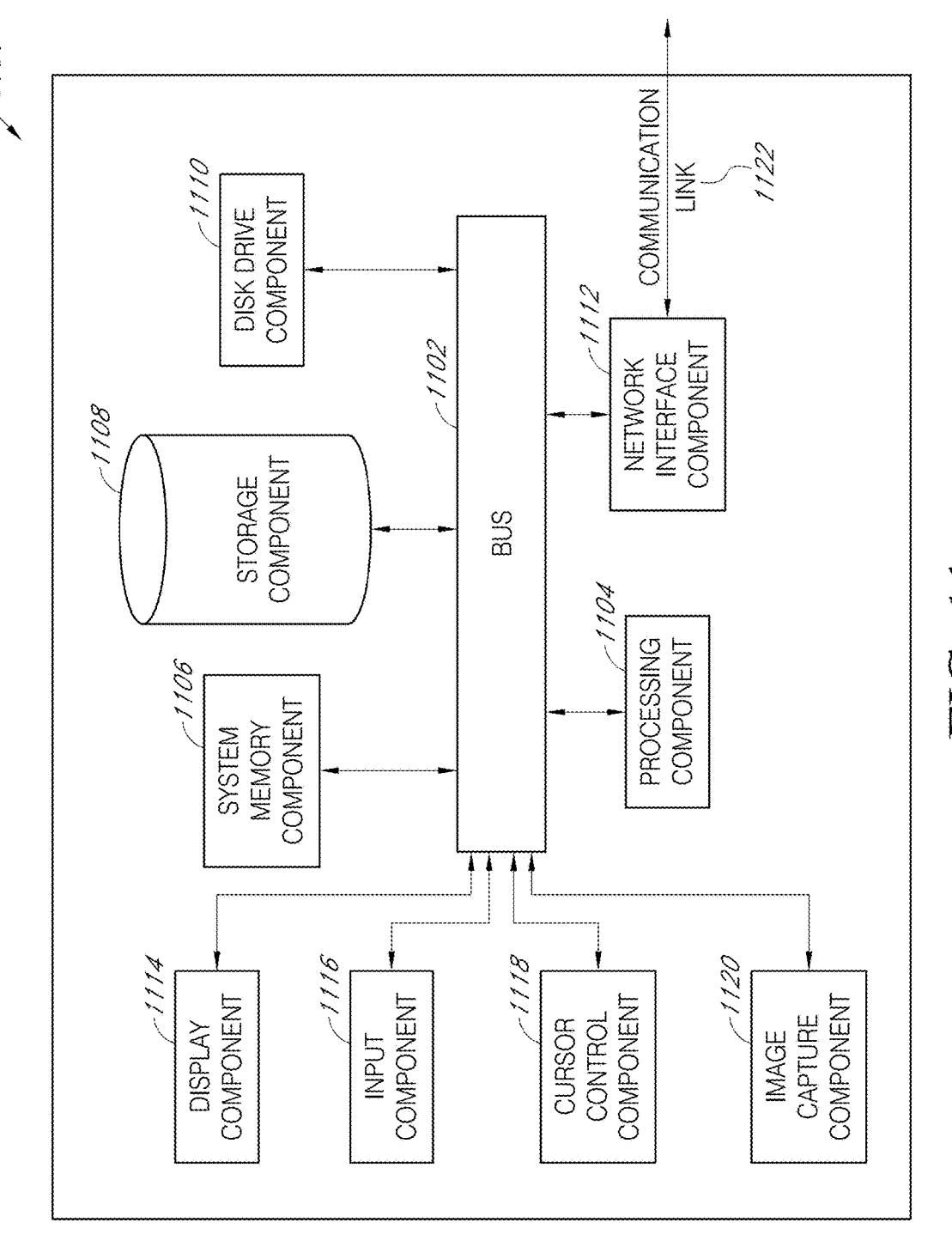
FIG. 11 is a block diagram of a computer system in accordance with various embodiments.

FIG. 11 is a block diagram of a computer system 1100 suitable for implementing various methods and devices described herein, for example, the lesion evaluation system 100, the computing platform 102, the data storage 104, the display system 106, the image processor 108, and/or the like. In various implementations, the devices capable of performing the steps may comprise a network communications device (e.g., mobile cellular phone, laptop, personal computer, tablet, etc.), a network computing device (e.g., a network server, a computer processor, a developer workstation, an electronic communications interface, etc.), or another suitable device. Accordingly, it should be appreciated that the devices capable of implementing the aforementioned servers, systems, and modules, and the various method steps of the method 200 discussed above may be implemented as the computer system 1100 in a manner as follows.

In accordance with various embodiments of the present disclosure, the computer system 1100, such as a network server, a workstation, a computing device, a communications device, etc., includes a bus component 1102 or other communication mechanisms for communicating information, which interconnects subsystems and components, such as a computer processing component 1104 (e.g., processor, micro-controller, digital signal processor (DSP), etc.), system memory component 1106 (e.g., RAM), static storage component 1108 (e.g., ROM), disk drive component 1110 (e.g., magnetic or optical), network interface component 1112 (e.g., modem or Ethernet card), display component 1114 (e.g., cathode ray tube (CRT) or liquid crystal display (LCD)), input component 1116 (e.g., keyboard), cursor control component 1118 (e.g., mouse or trackball), and image capture component 1120 (e.g., analog or digital camera). In one implementation, disk drive component 1110 may comprise a database having one or more disk drive components.

In accordance with embodiments of the present disclosure, computer system 1100 performs specific operations by the processor 1104 executing one or more sequences of one or more instructions contained in system memory component 1106. Such instructions may be read into system memory component 1106 from another computer readable medium, such as static storage component 1108 or disk drive component 1110. In other embodiments, hard-wired circuitry may be used in place of (or in combination with) software instructions to implement the present disclosure. In some embodiments, the various components of the lesion evaluation system 100, the computing platform 102, the data storage 104, the display system 106, the image processor 108, etc., may be in the form of software instructions that can be executed by the processor 1104 to automatically perform context-appropriate tasks on behalf of a user.

Logic may be encoded in a computer readable medium, which may refer to any medium that participates in providing instructions to the processor 1104 for execution. Such a medium may take many forms, including but not limited to, non-volatile media and volatile media. In one embodiment, the computer readable medium is non-transitory. In various implementations, non-volatile media includes optical or magnetic disks, such as disk drive component 1110, and volatile media includes dynamic memory, such as system memory component 1106. In one aspect, data and information related to execution instructions may be transmitted to computer system 1100 via a transmission media, such as in the form of acoustic or light waves, including those generated during radio wave and infrared data communications. In various implementations, transmission media may include coaxial cables, copper wire, and fiber optics, including wires that comprise bus 1102.

Some common forms of computer readable media include, for example, floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, carrier wave, or any other medium from which a computer is adapted to read. These computer readable media may also be used to store the programming code for the lesion evaluation system 100, the computing platform 102, the data storage 104, the display system 106, the image processor 108, etc., discussed above.

In various embodiments of the present disclosure, execution of instruction sequences to practice the present disclosure may be performed by computer system 1100. In various other embodiments of the present disclosure, a plurality of computer systems 1100 coupled by communication link 1122 (e.g., a communications network, such as a LAN, WLAN, PTSN, and/or various other wired or wireless networks, including telecommunications, mobile, and cellular phone networks) may perform instruction sequences to practice the present disclosure in coordination with one another.

Computer system 1100 may transmit and receive messages, data, information and instructions, including one or more programs (i.e., application code) through communication link 1122 and communication interface 1112. Received program code may be executed by computer processor 1104 as received and/or stored in disk drive component 1110 or some other non-volatile storage component for execution. The communication link 1122 and/or the communication interface 1112 may be used to conduct electronic communications between the lesion evaluation system 100, the computing platform 102, the data storage 104, the display system 106, the image processor 108 etc., for example.

Where applicable, various embodiments provided by the present disclosure may be implemented using hardware, software, or combinations of hardware and software. Also, where applicable, the various hardware components and/or software components set forth herein may be combined into composite components comprising software, hardware, and/or both without departing from the spirit of the present disclosure. Where applicable, the various hardware components and/or software components set forth herein may be separated into sub-components comprising software, hardware, or both without departing from the scope of the present disclosure. In addition, where applicable, it is contemplated that software components may be implemented as hardware components and vice-versa.

Software, in accordance with the present disclosure, such as computer program code and/or data, may be stored on one or more computer readable mediums. It is also contemplated that software identified herein may be implemented using one or more general purpose or specific purpose computers and/or computer systems, networked and/or otherwise. Where applicable, the ordering of various steps described herein may be changed, combined into composite steps, and/or separated into sub-steps to provide features described herein. It is understood that at least a portion of the lesion evaluation system 100, the computing platform 102, the data storage 104, the display system 106, the image processor 108, etc., may be implemented as such software code.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

In describing the various embodiments, the specification may have presented a method and/or process as a particular sequence of steps. However, to the extent that the method or process does not rely on the particular order of steps set forth herein, the method or process should not be limited to the particular sequence of steps described, and one skilled in the art can readily appreciate that the sequences may be varied and still remain within the spirit and scope of the various embodiments.

VII. Recitations of Various Embodiments of the Present Disclosure

Embodiment 1: A method, comprising: receiving a set of fundus autofluorescence (FAF) images of a retina having one or more geographic atrophy (GA) lesions; receiving one or both of a set of infrared (IR) images of the retina or a set of optical coherence tomography (OCT) images of the retina; and generating, using the set of FAF images and the one or both of the set of IR images or the set of OCT images, a GA lesion segmentation mask including one or more GA lesion segments corresponding to the one or more GA lesions in the retina.

Embodiment 2: The method of embodiment 1, further comprising extracting, by a processor, a feature of the one or more GA lesions in the retina from the GA lesion segmentation mask.

Embodiment 3: The method of embodiment 2, further comprising: generating, by the processor, a recommendation for treating the one or more GA lesions based on the extracted feature.

Embodiment 4: The method of embodiment 2 or 3, wherein the extracted feature includes a number of the one or more GA lesions.

Embodiment 5: The method of any of embodiments 2-4, further comprising: combining, by the processor, the one or more GA lesion segments into a single lesion component, the extracted feature including one or more of an area, a perimeter, a Feret diameter, or an excess rim intensity, of the single lesion component.

Embodiment 6: The method of any of embodiments 1-5, wherein the generating includes generating the GA lesion segmentation mask using a neural network, the neural network including a U-Net deep learning neural network having an encoder and a decoder.

Embodiment 7: The method of embodiment 6, further comprising generating, using the encoder, an encoded image input by concatenating the set of FAF images and the one or both of the set of IR images or the set of OCT images.

Embodiment 8: The method of embodiment 7, wherein the generating the GA lesion segmentation mask includes decoding the encoded image input using the decoder of the U-Net deep learning neural network.

Embodiment 9: The method of any of embodiments 1-8, wherein the generating includes generating the GA lesion segmentation mask using a neural network, the neural network including a Y-Net deep learning neural network having a first encoder, one or both of a second encoder or a third encoder, and a decoder.

Embodiment 10: The method of embodiment 9, further comprising: generating, via the first encoder and using the set of FAF images, an encoded FAF image input; and performing one or both of: generating, via the second encoder, encoded IR image input from the set of IR images; or generating, via the third encoder, encoded OCT image input from the set of OCT images.

Embodiment 11: The method of embodiment 10, further comprising: generating an encoded image input by concatenating the encoded FAF image input and one or both of the encoded IR image input or the encoded OCT image input; and the generating the GA lesion segmentation mask includes decoding the encoded image input using the decoder of the Y-Net deep learning neural network.

Embodiment 12: A system comprising: a non-transitory memory; and a hardware processor coupled with the non-transitory memory and configured to read instructions from the non-transitory memory to cause the system to perform the methods of embodiments 1-11.

Embodiment 13: A non-transitory computer-readable medium (CRM) having program code recorded thereon, the program code comprises code for causing a system to perform the methods of embodiments 1-11.

What is claimed is:

1. A method, comprising:
receiving a set of fundus autofluorescence (FAF) images of a retina having one or more geographic atrophy (GA) lesions;
receiving at least one of a set of infrared (IR) images of the retina or a set of optical coherence tomography (OCT) images of the retina; and
generating, using the set of FAF images and the at least one of the set of IR images or the set of OCT images, a GA lesion segmentation mask including one or more GA lesion segments corresponding to the one or more GA lesions in the retina.

2. The method of claim 1, further comprising:
extracting, by a processor, a feature of the one or more GA lesions in the retina from the GA lesion segmentation mask.

3. The method of claim 2, further comprising:
generating, by the processor, a recommendation for treating the one or more GA lesions based on the extracted feature.

4. The method of claim 2, wherein the extracted feature includes a number of the one or more GA lesions.

5. The method of claim 2, further comprising:
combining, by the processor, the one or more GA lesion segments into a single lesion component, the extracted feature including one or more of an area, a perimeter, a Feret diameter, or an excess rim intensity, of the single lesion component.

6. The method of claim 1, wherein the generating includes generating the GA lesion segmentation mask using a neural network, the neural network including a U-Net deep learning neural network having an encoder and a decoder.

7. The method of claim 6, further comprising:
generating, using the encoder, an encoded image input by concatenating the set of FAF images and the at least one of the set of IR images or the set of OCT images.

8. The method of claim 7, wherein the generating the GA lesion segmentation mask includes decoding the encoded image input using the decoder of the U-Net deep learning neural network.

9. The method of claim 8,
wherein both the set of IR images and the set of OCT images are received; and
wherein the GA lesion segmentation mask is generated using the set of FAF images, the set of IR images, and the set of OCT images.

10. The method of claim 1, wherein the generating includes generating the GA lesion segmentation mask using a neural network, the neural network including a Y-Net deep learning neural network having a first encoder, at least one of a second encoder for use in processing of the set of IR images or a third encoder for use in processing of the set of OCT images, and a decoder.

11. The method of claim 10, further comprising:
generating, via the first encoder and using the set of FAF images, an encoded FAF image input; and
performing:

generating, via the second encoder when the neural network includes the second encoder and the set of IR images is received, encoded IR image input from the set of IR images; or
generating, via the third encoder when the neural network includes the third encoder and the set of OCT images is received, encoded OCT image input from the set of OCT images.

12. The method of claim 11, further comprising:
generating an encoded image input by concatenating the encoded FAF image input, the encoded IR image input when the encoded IR image input has been generated, and the encoded OCT image input when the encoded OCT image input has been generated; and
the generating the GA lesion segmentation mask includes decoding the encoded image input using the decoder of the Y-Net deep learning neural network.

13. The method of claim 11,
wherein both the set of IR images and the set of OCT images are received; and
wherein the GA lesion segmentation mask is generated using the set of FAF images, the set of IR images, and the set of OCT images.

14. The method of claim 1,
wherein the set of IR images of the retina is received; and
wherein the GA lesion segmentation mask is generated using the set of FAF images and the set of IR images.

15. The method of claim 1,
wherein the set of OCT images is received; and
wherein the GA lesion segmentation mask is generated using the set of FAF images and the set of OCT images.

16. The method of claim 1,
wherein both the set of IR images and the set of OCT images are received; and
wherein the GA lesion segmentation mask is generated using the set of FAF images, the set of IR images, and the set of OCT images.

17. The method of claim 8,
wherein the generating includes generating the GA lesion segmentation mask using a neural network; and
wherein the neural network was trained using a training set comprising: FAF images and IR images; FAF images and OCT images; or FAF images, IR images, and OCT images.

18. A system, comprising:
a non-transitory memory; and
a hardware processor coupled with the non-transitory memory and configured to read instructions from the non-transitory memory to cause the system to perform operations comprising:
receiving a set of fundus autofluorescence (FAF) images of a retina having one or more geographic atrophy (GA) lesions;
receiving at least one of a set of infrared (IR) images of the retina or a set of optical coherence tomography (OCT) images of the retina; and
generating, using the set of FAF images and the at least one of the set of IR images or the set of OCT images, a GA lesion segmentation mask including one or more GA lesion segments corresponding to the one or more GA lesions in the retina.

19. The system of claim 18, wherein the processor is further configured to extract a feature of the one or more GA lesions in the retina from the GA lesion segmentation mask.

20. The system of claim 19, wherein the feature includes a number of the one or more GA lesions, an area of a single lesion component wherein the one or more GA lesions are combined into the single lesion component, a perimeter of the single lesion component, a Feret diameter of the single lesion component, or an excess rim intensity of the single lesion component.

21. The system of claim 19, wherein the processor is further configured to generate a recommendation for treating the one or more GA lesions based on the extracted feature.

22. The system of claim 18, wherein the processor is configured to generate the GA lesion segmentation mask using a neural network, the neural network including a U-Net deep learning neural network having an encoder and a decoder.

23. The system of claim 22, wherein the U-Net deep learning neural network is further configured to:
   generate, via the encoder, an encoded image input by concatenating the set of FAF images and the at least one of the set of IR images or the set of OCT images; and
   generate, via the decoder, the GA lesion segmentation mask by decoding the encoded image input.

24. The system of claim 18, wherein the processor is configured to generate the GA lesion segmentation mask using a neural network, the neural network including a Y-Net deep learning neural network including a first encoder, at least one of a second encoder for use in processing of the set of IR images or a third encoder for use in processing of the set of OCT images, and a decoder.

25. The system of claim 24, wherein the Y-Net deep learning neural network is further configured to:
   generate, via the first encoder and using the set of FAF images, an encoded FAF image input;
   perform:
      generate, via the second encoder when the neural network includes the second encoder and the set of IR images is received, encoded IR image input from the set of IR images; or
      generate, via the third encoder when the neural network includes the third encoder and the set of OCT images is received, encoded OCT image input from the set of OCT images; and
   generate, via the decoder, the GA lesion segmentation mask by decoding the encoded image input.

26. The system of claim 18,
   wherein the set of IR images of the retina is received; and
   wherein the GA lesion segmentation mask is generated using the set of FAF images and the set of IR images.

27. The system of claim 18,
   wherein the set of OCT images is received; and
   wherein the GA lesion segmentation mask is generated using the set of FAF images and the set of OCT images.

28. The system of claim 18,
   wherein both the set of IR images and the set of OCT images are received; and
   wherein the GA lesion segmentation mask is generated using the set of FAF images, the set of IR images, and the set of OCT images.

29. The system of claim 18,
   wherein both the set of IR images and the set of OCT images are received; and
   wherein the GA lesion segmentation mask is generated using the set of FAF images, the set of IR images, and the set of OCT images.

30. The system of claim 18,
   wherein both the set of IR images and the set of OCT images are received; and wherein the GA lesion segmentation mask is generated using the set of FAF images, the set of IR images, and the set of OCT images.

31. The system of claim 18,
   wherein the generating includes generating the GA lesion segmentation mask using a neural network; and
   wherein the neural network was trained using a training set comprising: FAF images and IR images; FAF images and OCT images; or FAF images, IR images, and OCT images.

32. A non-transitory computer-readable medium (CRM) having stored thereon computer-readable instructions executable to cause a computer system to perform operations comprising:
   receiving a set of fundus autofluorescence (FAF) images of a retina having one or more geographic atrophy (GA) lesions;
   receiving a set of infrared (IR) images of the retina and a set of optical coherence tomography (OCT) images of the retina; and
   generating, using the set of FAF images, the set of IR images, and the set of OCT images, a GA lesion segmentation mask including one or more GA lesion segments corresponding to the one or more GA lesions in the retina.

33. The non-transitory computer-readable medium of claim 32,
   wherein the set of IR images of the retina is received; and
   wherein the GA lesion segmentation mask is generated using the set of FAF images and the set of IR images.

34. The non-transitory computer-readable medium of claim 32,
   wherein the set of OCT images is received; and
   wherein the GA lesion segmentation mask is generated using the set of FAF images and the set of OCT images.

35. The non-transitory computer-readable medium of claim 32,
   wherein both the set of IR images and the set of OCT images are received; and
   wherein the GA lesion segmentation mask is generated using the set of FAF images, the set of IR images, and the set of OCT images.

36. The non-transitory computer-readable medium of claim 32,
   wherein both the set of IR images and the set of OCT images are received; and
   wherein the GA lesion segmentation mask is generated using the set of FAF images, the set of IR images, and the set of OCT images.

37. The non-transitory computer-readable medium of claim 32,
   wherein both the set of IR images and the set of OCT images are received; and
   wherein the GA lesion segmentation mask is generated using the set of FAF images, the set of IR images, and the set of OCT images.

38. The non-transitory computer-readable medium of claim 32,
   wherein the generating includes generating the GA lesion segmentation mask using a neural network; and
   wherein the neural network was trained using a training set comprising: FAF images and IR images; FAF images and OCT images; or FAF images, IR images, and OCT images.

* * * * *